(12) United States Patent
Galley et al.

(10) Patent No.: US 9,181,230 B2
(45) Date of Patent: Nov. 10, 2015

(54) MORPHOLINE COMPOUNDS AND USES THEREOF

(71) Applicant: Hoffmann-La Roche Inc., Little Falls, NJ (US)

(72) Inventors: Guido Galley, Rheinfelden (DE); Annick Goergler, Colmar (FR); Roger Norcross, Olsberg (CH); Philippe Pflieger, Schwoben (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/328,398

(22) PCT Filed: Jan. 8, 2013

(86) PCT No.: PCT/EP2013/050170
§ 371 (c)(1),
(2) Date: Jul. 10, 2014

(87) PCT Pub. No.: WO2013/104591
PCT Pub. Date: Jul. 18, 2013

(65) Prior Publication Data
US 2015/0045359 A1     Feb. 12, 2015

(51) Int. Cl.
*A61K 31/535* (2006.01)
*C07D 413/10* (2006.01)
*C07D 413/14* (2006.01)
*C07D 471/04* (2006.01)
*C07D 487/04* (2006.01)

(52) U.S. Cl.
CPC ............ *C07D 413/10* (2013.01); *C07D 413/14* (2013.01); *C07D 471/04* (2013.01); *C07D 487/04* (2013.01)

(58) Field of Classification Search
USPC ............. 514/234.2, 234.5, 234; 544/139, 140
See application file for complete search history.

(56) References Cited

FOREIGN PATENT DOCUMENTS

| WO | WO 97/12874 A1 | 10/1997 |
|---|---|---|
| WO | WO 02/76950 A2 | 3/2002 |
| WO | WO 02/76950 A3 | 3/2002 |
| WO | 2009/035159 A1 | 3/2009 |
| WO | WO 2009/019149 A1 | 12/2009 |
| WO | 2011/076678 A1 | 6/2011 |
| WO | 2012/004375 A1 | 1/2012 |
| WO | 2012/016879 A1 | 2/2012 |
| WO | 2012/126922 A1 | 9/2012 |
| WO | 2012/168260 A1 | 12/2012 |
| WO | 2012/168265 A1 | 12/2012 |

OTHER PUBLICATIONS

International Preliminary Report on Patentability (Jul. 15, 2014) for International Patent Application No. PCT/EP2013/050170, in 6 pages.
International Search Report for International Patent Application No. PCT/EP2013/050170, mailed Mar. 6, 2013, in 3 pages.

*Primary Examiner* — Rei-Tsang Shiao
(74) *Attorney, Agent, or Firm* — Brian L. Buckwalter

(57) ABSTRACT

The present invention relates to compounds of formula

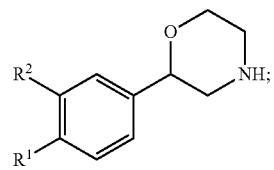

(I)

wherein $R^1$ and $R^2$ are as described herein. Compounds of the invention are useful in the treatment and/or prophylaxis of diseases associated with TAAR modulation.

21 Claims, No Drawings

MORPHOLINE COMPOUNDS AND USES THEREOF

CROSS-REFERENCE TO RELATED APPLICATIONS

This application is a continuation application and claims priority under 35 U.S.C. 365(c) to International Application No. PCT/EP2013/050170, filed on Jan. 8, 2013, which claims priority EP Application No. 12150876.6 filed on Jan. 12, 2012. The entire content of the applications referenced above are hereby incorporated by reference herein.

BACKGROUND OF THE INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9, 12, 13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gas. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors. Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. The present invention fulfills at least this need.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol.* 1: *Trace Amines and the Brain. [Proceedings of a Study Group at the* 14*th Annual Meeting of the American College of Neuropsychoparmacology,* San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

In one aspect, the present invention relates to compounds of formula

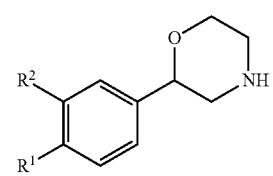

I wherein

R¹ is a one or two membered heteroaryl group, selected from the group consisting of a) 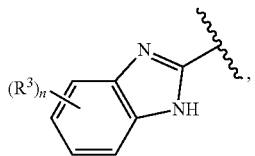

b) 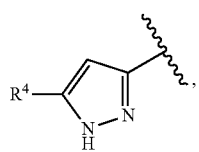

c) 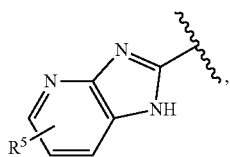

d) 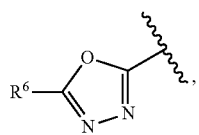

e) 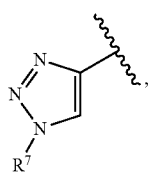

f) 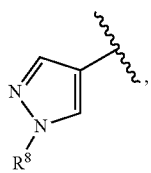

g) 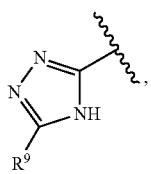

h) 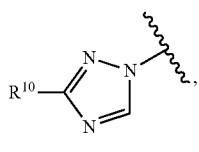

i) 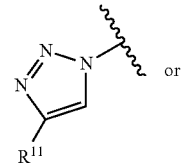 or j) 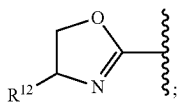

R² is hydrogen or halogen; or
R¹ and R² may form together with the carbon atoms to with they are attached the following rings k) 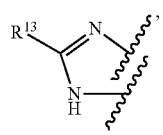

l) 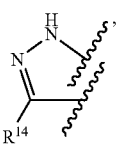

m) 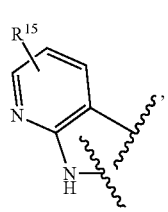

n) 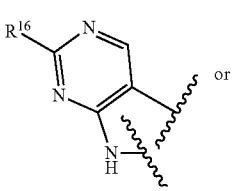 or o) 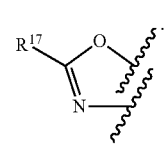

R³ is hydrogen, halogen or lower alkyl;
n is 1 or 2;
R⁴ is phenyl, optionally substituted by one or two substituents, selected from halogen or cyano, or is pyridinyl, optionally substituted by halogen, or is tetrahydropyran, or is
—NH—C(O)-phenyl, optionally substituted by halogen;
R⁵ is hydrogen or halogen;
R⁶-R¹³ are phenyl, optionally substituted by halogen;
R¹⁴ is —NH—C(O)-phenyl, substituted by halogen;
R¹⁵ is hydrogen, lower alkyl substituted by halogen or is halogen;
R¹⁶ is hydrogen or lower alkoxy;
R¹⁷ is pyridinyl, optionally substituted by lower alkoxy or lower alkyl substituted by halogen;
or to a pharmaceutically suitable acid addition salt thereof, to all racemic mixtures, to all their corresponding enantiomers and/or optical isomers and to all tautomeric forms of compounds of formula I.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

In one embodiment, It has now been found that the compounds of formula I have a good affinity to the trace amine associated receptors (TAARs), especially for TAAR1.

In another embodiment, the compounds may be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

In another embodiment, objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, attention deficit hyperactivity disorder (ADHD) and diabetes.

DEFINITIONS

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are $CF_3$, $CHF_2$, $CH_2F$, $CH_2CF_3$ or $CH_2CHF_2$.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

A racemic mixture or racemate is one that has equal amounts of left- and right-handed enantiomers of a chiral molecule.

An enantiomer is one of two sterioisomers that are mirror images of each other.

Tautomers are isomers of organic compounds that readily interconvert by a chemical reaction. This reaction commonly results in the formal migration of a hydrogen atom or proton, accompanied by a switch of a single bond and adjacent double bond. Because of the rapid interconversion, tautomers are generally considered to be the same chemical compound.

Compounds

In one aspect the present inventions provides for compounds of Formula I as described hereinabove.

The embodiments of the present invention are the following structures:

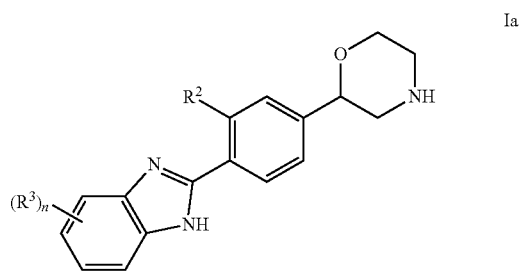

Ia

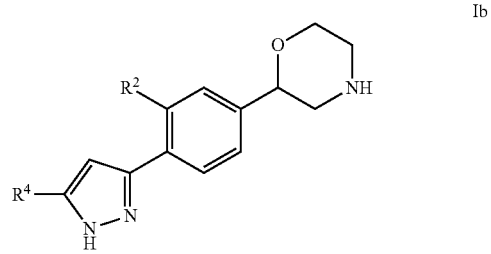

Ib

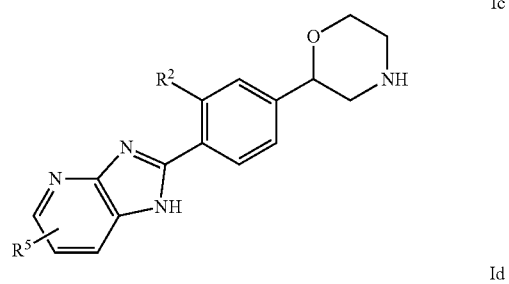

Ic

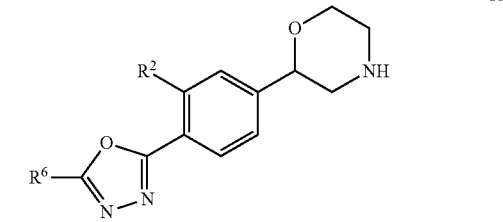

Id

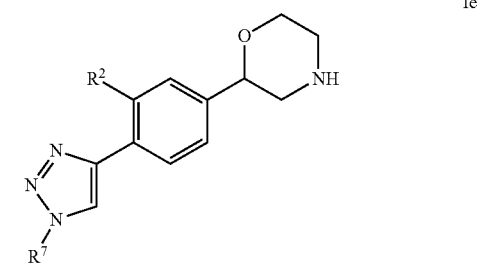

Ie

-continued

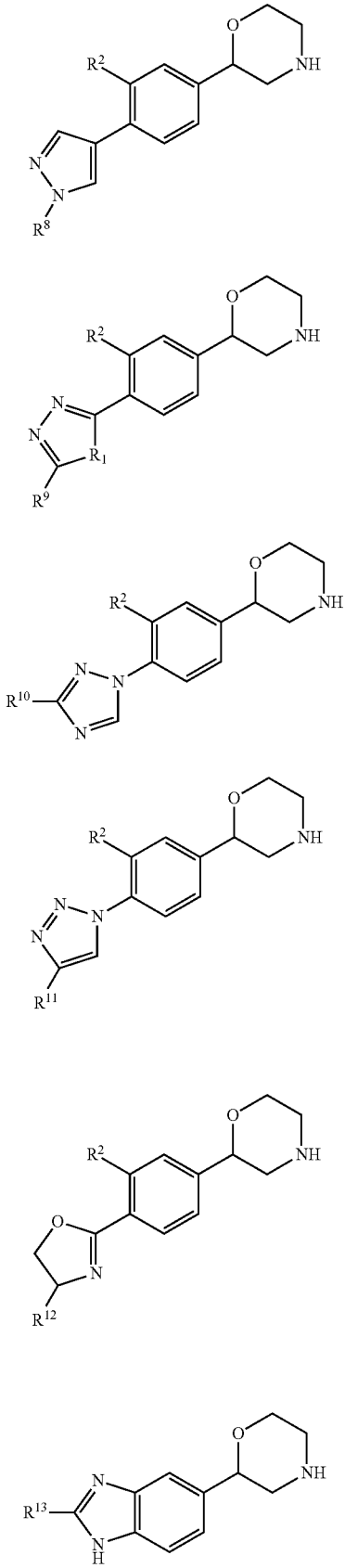

f)
Ig
Ih
Ii
Ij
Ik

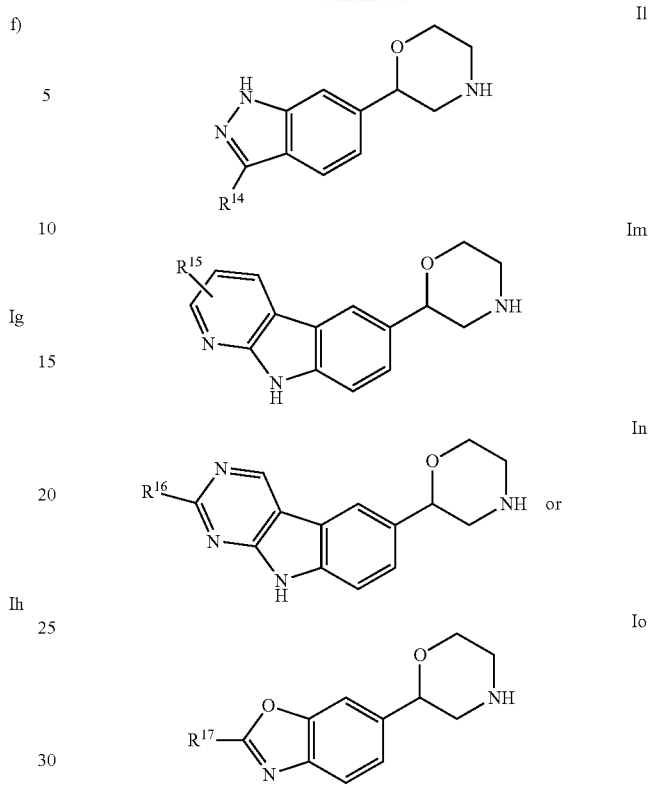

Il
5
10  Im
15
20  In or
Ih
25
30  Io wherein
R² is hydrogen or halogen; or
R³ is hydrogen, halogen or lower alkyl;
n is 1 or 2;
R⁴ is phenyl, optionally substituted by one or two substituents, selected from halogen or cyano, or is
pyridinyl, optionally substituted by halogen, or is
tetrahydropyran, or is
—NH—C(O)-phenyl, optionally substituted by halogen;
R⁵ is hydrogen or halogen;
R⁶-R¹³ are phenyl, optionally substituted by halogen:
R¹⁴ is —NH—C(O)-phenyl, substituted by halogen;
R¹⁵ is hydrogen, lower alkyl substituted by halogen or halogen; and
R¹⁶ is hydrogen or lower alkoxy;
R¹⁷ is pyridinyl, optionally substituted by lower alkoxy or lower alkyl substituted by halogen;
or a pharmaceutically suitable acid addition salt thereof, all racemic mixtures, all their corresponding enantiomers and/or optical isomers and all tautomeric forms of compounds of formula I.

Compounds of Formula Ia are:
2-(4-(1H-Benzo[d]imidazol-2-yl)phenyl)morpholine
2-(4-(6-Chloro-1H-benzo[d]imidazol-2-yl)phenyl)morpholine
(S)-2-(4-(6-Fluoro-1H-benzo[d]imidazol-2-yl)phenyl)morpholine
(S)-2-(4-(4,6-Difluoro-1H-benzo[d]imidazol-2-yl)phenyl)morpholine
(R)-2-(4-(6-Fluoro-1H-benzo[d]imidazol-2-yl)phenyl)morpholine or
(S)-2-(4-(5,6-Dimethyl-1H-benzo[d]imidazol-2-yl)phenyl)morpholine.

Compounds of Formula Ib are:
2-(4-(5-(4-Chlorophenyl)-1H-pyrazol-3-yl)phenyl)morpholine
2-(4-(5-(4-Fluorophenyl)-1H-pyrazol-3-yl)phenyl)morpholine 2-(4-(5-(6-Chloropyridin-3-yl)-1H-pyrazol-3-yl)phenyl)
morpholine
4-(3-(4-(Morpholin-2-yl)phenyl)-1H-pyrazol-5-yl)benzonitrile
(R)-2-(4-(5-(3-Chlorophenyl)-1H-pyrazol-3-yl)phenyl)morpholine
(S)-2-(4-(5-(3-Chlorophenyl)-1H-pyrazol-3-yl)phenyl)morpholine
3-[5-(4-Morpholin-2-yl-phenyl)-2H-pyrazol-3-yl]-benzonitrile
(S)-2-(4-(5-(2,4-Difluorophenyl)-1H-pyrazol-3-yl)phenyl)
morpholine
(R)-2-(4-(5-(2,4-Difluorophenyl)-1H-pyrazol-3-yl)phenyl)
morpholine
(S)-2-(4-(5-(Tetrahydro-2H-pyran-4-yl)-1H-pyrazol-3-yl)
phenyl)morpholine
(S)-4-(3-(4-(Morpholin-2-yl)phenyl)-1H-pyrazol-5-yl)benzonitrile
(S)-2-(4-(5-(4-Fluorophenyl)-1H-pyrazol-3-yl)phenyl)morpholine
(S)-4-Fluoro-N-(3-(4-(morpholin-2-yl)phenyl)-1H-pyrazol-5-yl)benzamide
(R)-2-(4-(5-(4-Fluorophenyl)-1H-pyrazol-3-yl)phenyl)morpholine
(R)-4-(3-(4-(Morpholin-2-yl)phenyl)-1H-pyrazol-5-yl)benzonitrile
(S)-3-Fluoro-4-(3-(4-(morpholin-2-yl)phenyl)-1H-pyrazol-5-yl)benzonitrile
(S)-2-{4-[5-(6-Chloro-pyridin-3-yl)-1H-pyrazol-3-yl]-phenyl}-morpholine
(R)-2-{4-[5-(6-Chloro-pyridin-3-yl)-1H-pyrazol-3-yl]-phenyl}-morpholine
(S)-2-(3-Fluoro-4-(5-(4-fluorophenyl)-1H-pyrazol-3-yl)
phenyl)morpholine
(R)-2-(3-Fluoro-4-(5-(4-fluorophenyl)-1H-pyrazol-3-yl)
phenyl)morpholine or
(S)-2-(4-(5-(2-Chloropyridin-4-yl)-1H-pyrazol-3-yl)phenyl)morpholine.
A Compound of Formula Ic is:
(S)-2-(4-(6-bromo-1H-imidazo[4,5-b]pyridin-2-yl)phenyl)
morpholine.
Compounds of Formula Id are:
(S)-2-(4-(5-(4-Fluorophenyl)-1,3,4-oxadiazol-2-yl)phenyl)
morpholine or
(R)-2-(4-(5-(4-Fluorophenyl)-1,3,4-oxadiazol-2-yl)phenyl)
morpholine.
Compounds of Formula Ie are:
(S)-2-(4-(1-(4-Fluorophenyl)-1H-1,2,3-triazol-4-yl)phenyl)
morpholine or
(R)-2-(4-(1-(4-Fluorophenyl)-1H-1,2,3-triazol-4-yl)phenyl)
morpholine.
Compounds of Formula If are:
(S)-2-(4-(1-(4-Fluorophenyl)-1H-pyrazol-4-yl)phenyl)morpholine or
(R)-2-(4-(1-(4-Fluorophenyl)-1H-pyrazol-4-yl)phenyl)morpholine.
Compounds of Formula Ig are:
(S)-2-(4-(5-(4-Fluorophenyl)-1H-1,2,4-triazol-3-yl)phenyl)
morpholine or
(R)-2-(4-(5-(4-Fluorophenyl)-1H-1,2,4-triazol-3-yl)phenyl)
morpholine.
Compounds of Formula Ih are:
(S)-2-(4-(3-(4-Fluorophenyl)-1H-1,2,4-triazol-1-yl)phenyl)
morpholine or
(R)-2-(4-(3-(4-Fluorophenyl)-1H-1,2,4-triazol-1-yl)phenyl)
morpholine.
Compounds of Formula Ii are:
(S)-2-(4-(4-(4-Fluorophenyl)-1H-1,2,3-triazol-1-yl)phenyl)
morpholine or
(R)-2-(4-(4-(4-Fluorophenyl)-1H-1,2,3-triazol-1-yl)phenyl)
morpholine.

A Compound of Formula Ij is:
(S)-2-{4-[(R)-4-(4-Fluoro-phenyl)-4,5-dihydro-oxazol-2-yl]-phenyl}-morpholine.
Compounds of Formula Ik are:
(S)-2-(2-(4-Fluorophenyl)-1H-benzo[d]imidazol-5-yl)morpholine or
(R)-2-(2-(4-Fluorophenyl)-1H-benzo[d]imidazol-5-yl)morpholine.
A Compound of Formula Il is:
4-Fluoro-N-(6-(morpholin-2-yl)-1H-indazol-3-yl)benzamide.
Compounds of Formula Im are:
(S)-2-(9H-Pyrido[2,3-b]indol-6-yl)morpholine
(S)-2-(3-(Trifluoromethyl)-9H-pyrido[2,3-b]indol-6-yl)
morpholine
(S)-2-(3-Chloro-9H-pyrido[2,3-b]indol-6-yl)morpholine
(R)-2-(3-(Trifluoromethyl)-9H-pyrido[2,3-b]indol-6-yl)
morpholine
(S)-2-(2-(Trifluoromethyl)-9H-pyrido[2,3-b]indol-6-yl)
morpholine or
(R)-2-(3-(Trifluoromethyl)-9H-pyrido[2,3-b]indol-6-yl)
morpholine.
A Compound of Formula In is:
(S)-2-(2-Isopropoxy-9H-pyrimido[4,5-b]indol-6-yl)morpholine.
Compounds of Formula Io are
(R)-2-(6-Ethoxypyridin-3-yl)-6-(morpholin-2-yl)benzo[d]
oxazole
(R)-6-(Morpholin-2-yl)-2-(6-(trifluoromethyl)pyridin-3-yl)
benzo[d]oxazole
(R)-6-(Morpholin-2-yl)-2-(2-(trifluoromethyl)pyridin-4-yl)
benzo[d]oxazole or
(S)-6-(Morpholin-2-yl)-2-(2-(trifluoromethyl)pyridin-4-yl)
benzo[d]oxazole.

General Synthetic Schemes

The present compounds of formula I and their pharmaceutically acceptable salts can be prepared by methods known in the art, for example, by processes described below, which process comprises deprotecting a compound of formula

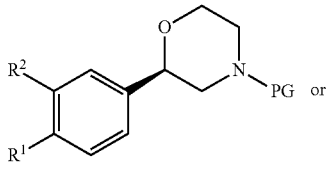

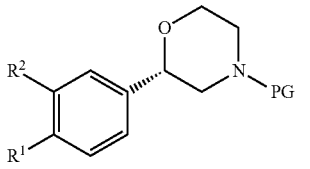

with HCl in dioxane for 2 hours at 60° C., or with CF$_3$COOH in dichloromethane at room temperature to a compound of formula

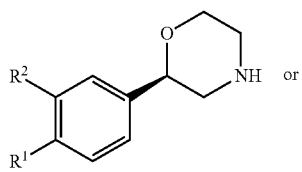

I-1

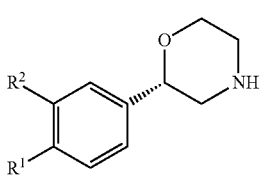

I-2 wherein PG is an acid labile amino protecting group, such as a tert-butoxycarbonyl group, and R¹ and R² are as described above and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following schemes 1-16 and in the description of 55 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1-16, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

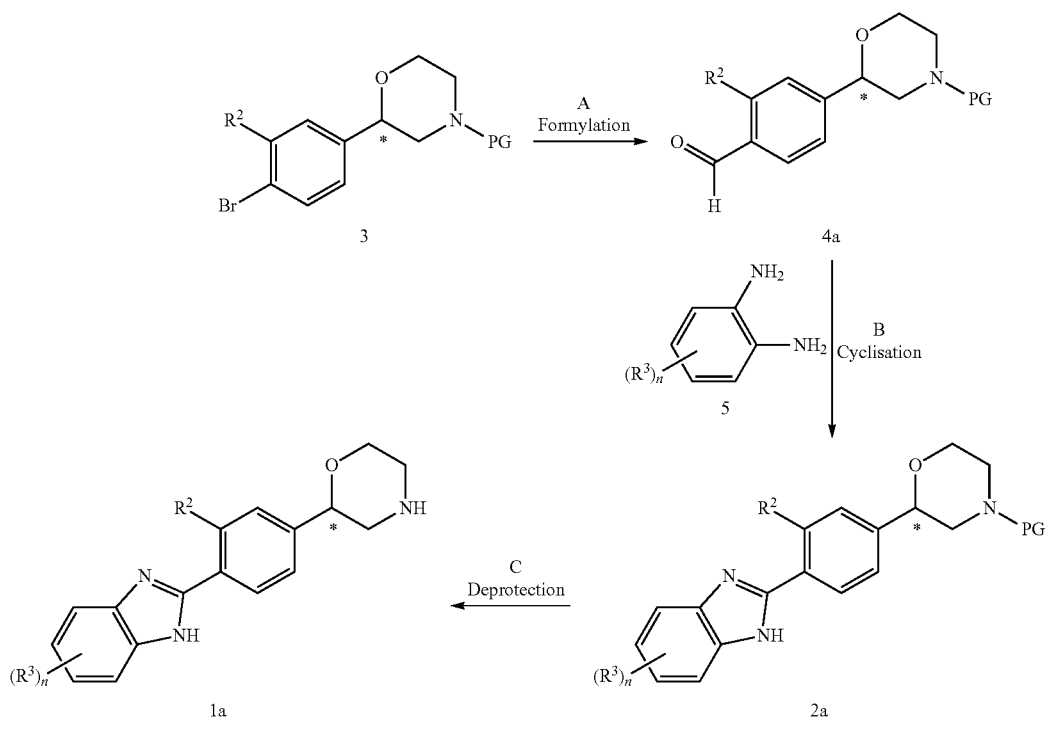

Scheme 1

* Stereochemistry can be R or S or racemic

Step A: The N-protected morpholine derivative 3 can be formylated by using an organometallic reagent such as n-butyl lithium or sec-butyl lithium or tert-butyl lithium in combination with dimethylformamide in a suitable solvent such as THF at temperatures from −78° C. to −10° C. for 1-18 hrs.

Preferred conditions are n-butyl lithium and dimethylformamide in THF at −78° C. for 2 hrs. A preferred protecting group PG is the tert-butoxycarbonyl group.

Step B: Cyclisation of the aldehyde 4a with 1,2-diaminoaryl compounds 5 can be accomplished by reacting these compounds in presence of an oxydating reagent such as sodium metabisulfite in a suitable solvent such as dimethylacetamide at temperatures from 0° C. to 100° C. for 1-24 hrs.

Preferred conditions are the use of sodium metabisulfite in dimethylacetamide at 90° C. for 18 hrs.

Step C: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

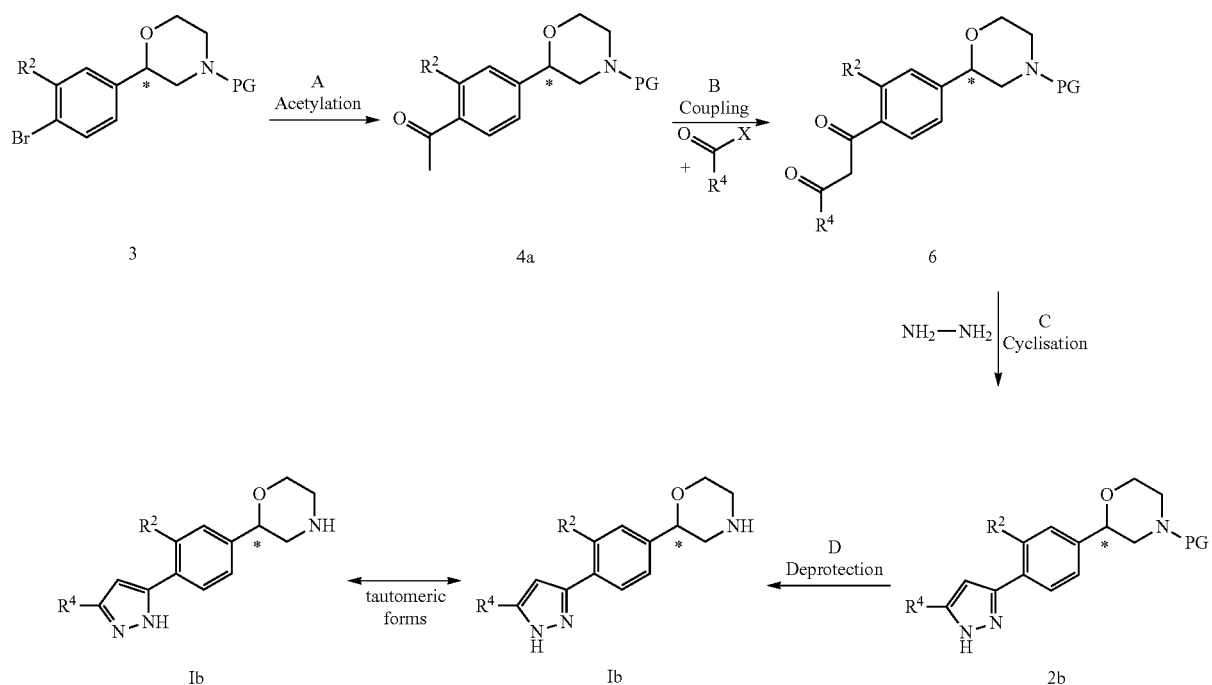

Scheme 2

* Stereochemistry can be R or S or racemic

X = halogen

Step A: The N-protected morpholine derivative 3 can be acetylated by using an organometallic reagent such as n-butyl lithium or sec-butyl lithium or tert-butyl lithium in combination with N-methoxy-N-methylacetamide or dimethylacetamide in a suitable solvent such as THF at temperatures from −78° C. to 0° C. for 1-18 hrs.

Preferred conditions are n-butyl lithium and N-methoxy-N-methylacetamide in THF at −78° C. for 1 h. A preferred protecting group PG is the tert-butoxycarbonyl group.

Step B: The acetyl compound 4a can be deprotonated with a base like lithium-bis-(trimethylsilyl)amide or lithiumdiisopropylamide in a suitable solvent such as THF and then further reacted with an acid chloride or ester VIII at temperatures from −78° C. to 0° C. for 1-18 hrs.

Preferred conditions are lithium-bis-(trimethylsilyl)amide and acid chloride in THF at −78° C. for 1 hrs.

Step C: The dicarbonyl compound 6 can be reacted with hydrazine or its hydrate in a suitable solvent such as ethanol, methanol n-propanol or isopropanol at 0 to 80° C. for 1-18 hrs.

Preferred conditions are reaction with hydrazine hydrate in ethanol at refux for 3-4 hrs.

Step D: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 3

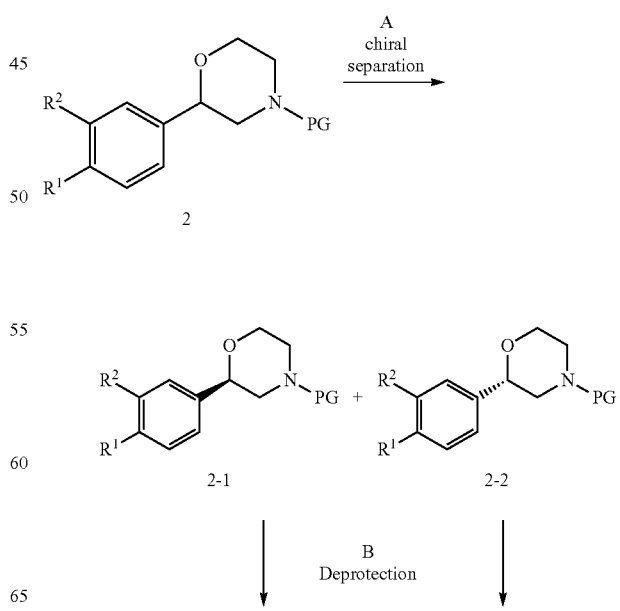

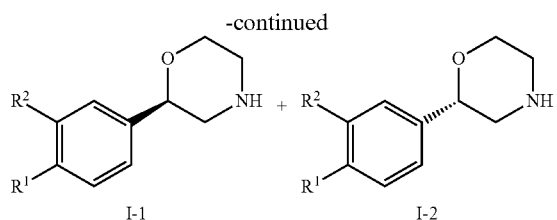

Step A: Protected morpholines 2 can be separated into their enantiomeric forms by chiral separation. Preferred protecting group is the tert-butoxycarbonyl group, a preferred chiral separation is the chiral chromatography using a chiral stationary phase such as Chiralpak AD and a suitable solvent such as a mixture of isopropanol and heptane.

Step B: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Step A: Reaction of aldehyde 4 with hydrazide 7 can be accomplished by stirring both components in a suitable solvent such as ethanol, methanol, THF or dichloromethane with or without a drying agent such as molecular sieves or magnesium sulfat at temperatures from 0° C. to 60° C.

Preferred conditions are stirring in ethanol at room temperature without drying reagent for 2 hrs.

Step B: Oxydative cyclisation can be achieved by treatment of 8 with an oxydating reagent, such as [bis(trifluoroacetoxy)iodo]benzene in a suitable solvent such as chloroform, dichloromethane, 1,2-dimethoxyethane, THF or diethylether at temperatures from −78° C. to reflux for 1-24 hrs.

Preferred conditions are treatment with [bis(trifluoroacetoxy)iodo]benzene for 20 min at room temperature.

Step C: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0° to 60° C.

Preferred conditions are the use of HCl in dioxane for 2 hrs at 60° C. or the use of $CF_3COOH$ in dichloromethane at room temperature overnight.

Scheme 4

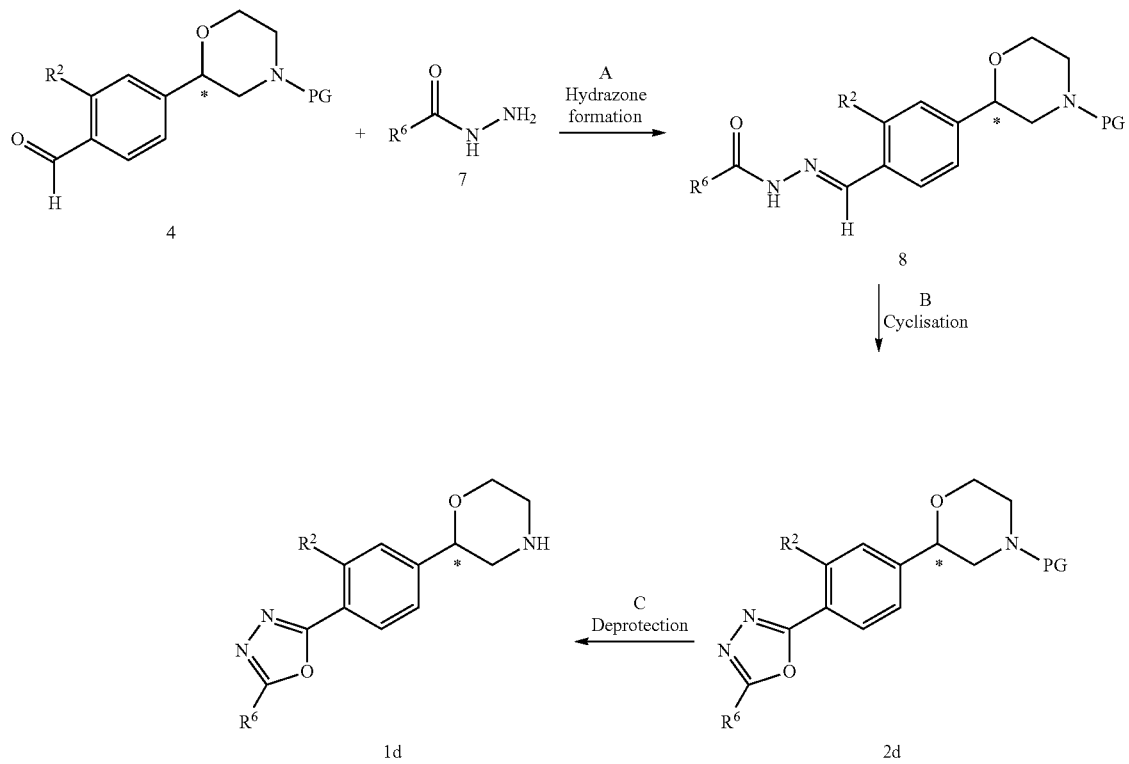

*Stereochemistry can be R or S or racemic

Scheme 5

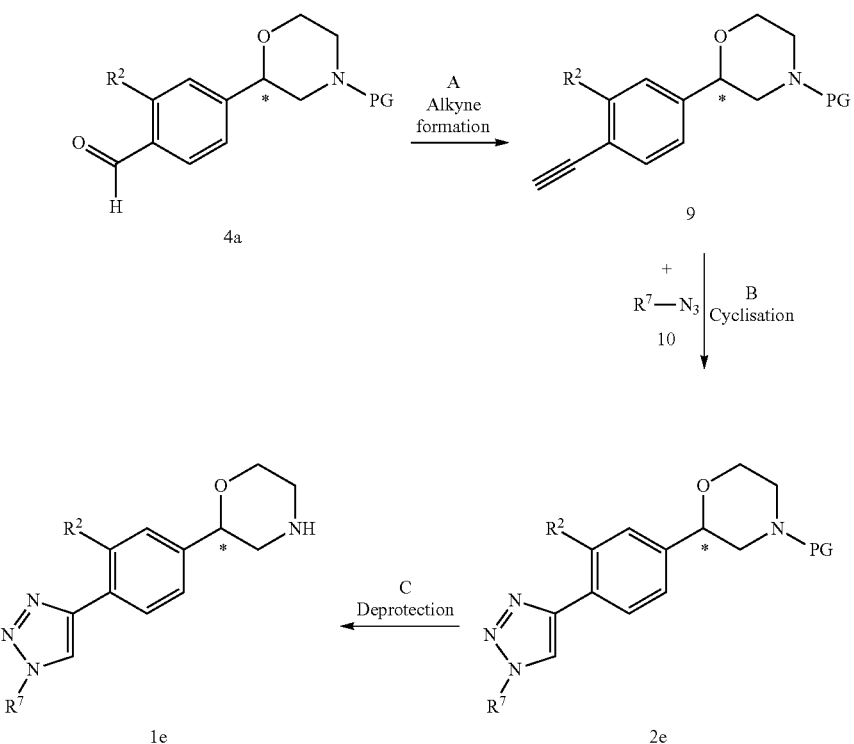

* Stereochemistry can be R or S or racemic

Step A: Alkyne formation can be accomplished by reaction of aldehyde 4a with a suitable reagent such as dimethyl 1-diazo-2-oxopropylphosphonate and a base such as potassium carbonate or sodium carbonate in a solvent such as methanol, ethanol or isopropanol at temperatures −20° C.-60° C. for 15 min-18 hrs. Alternatively, a reaction of aldehyde 4a with tetrabromomethane and triphenylphospine, followed by treatment with a strong base such as butyllithium can be used.

Preferred conditions are the use of dimethyl 1-diazo-2-oxopropylphosphonate and potassium carbonate in methanol at room temperature for 2 hrs.

Step B: Formation of the triazole can be achieved by reaction of the alkyne 9 with an azide 10 in a suitable solvent such as benzene, toluene, dichloromethane, tetrahydrofurane, pyridine, N,N-diisopropylamine or triethylamine with or without a catalyst such as copper salts at −20° C. to 60° C. for 15 min to 18 hrs.

Preferred conditions are the use of copper(I) iodide in N,N-diisopropylamine as solvent at room temperature for 3 hrs.

Step C: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 6

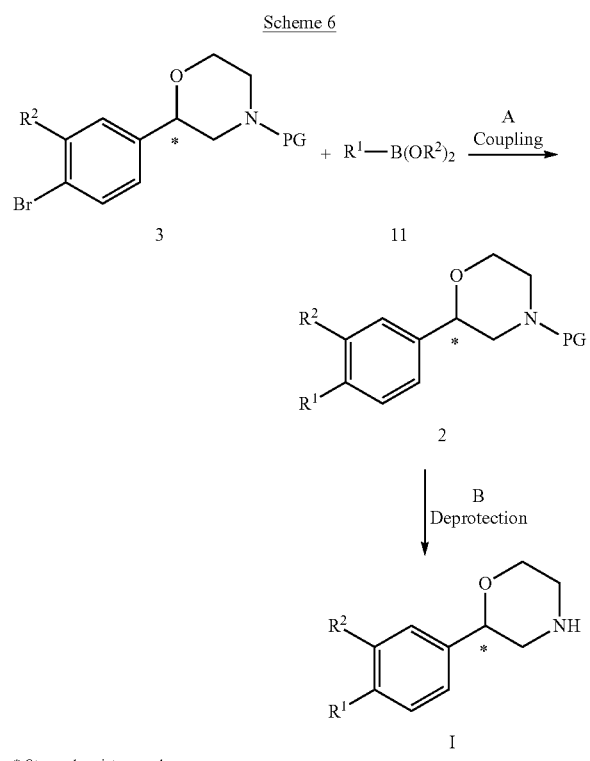

* Stereochemistry can be R or S or racemic

Step A: Coupling of the bromoderivative 3 with a suitable boronic acid or boronic acid ester 11 can be accomplished by using a palladium catalyst such as palladium(II)-acetate or palladium(II)-chloride or tetrakis(triphenylphosphine)palladium(0) in combination with a ligand such as triphenylphosphine, tricyclohexylphosphine or the like, and a base such as potassium phosphate, potassium carbonate, cesium carbonate, triethylamine or diisopropylethylamine in a suitable solvent such as dioxane, dimethylacetamide, dimethylformamide, tetrahydrofurane, dimethoxyethane, diglyme, ethanol, methanol or water at 20° C. to 180° C. for 5 min to 18 hrs with or without microwave irradiation.

Preferred conditions are the use of tetrakis(triphenylphosphine)palladium(0) and potassium phosphate in dimethylacetamide at 150° C. under microwave irradiation for 10 min.

Step B: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Step A: Nitrile formation can be accomplished by reaction of bromide 3 with a suitable reagent such as zinc zyanide and a catalyst such as or tetrakis(triphenylphosphine)palladium(0) in a solvent such as dimethylformamide at temperatures from 20° C.-120° C. for 1 h-24 hrs.

Preferred conditions are the use of zinc zyanide and tetrakis(triphenylphosphine)palladium(0) in dimethylformamide at 85° C. overnight.

Step B: Formation of the triazole can be achieved by reaction of the nitrile 12 with a hydrazide 13 in a suitable solvent such as ethanol, methanol, propanol or butan-1-ol with a suitable base such as potassium carbonate, sodium carbonate at 20° C. to 160° C. for 1 h to 24 hrs.

Preferred conditions are the use of potassium carbonate in butan-1-ol as solvent at 150° C. for 3 hrs.

Step C: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

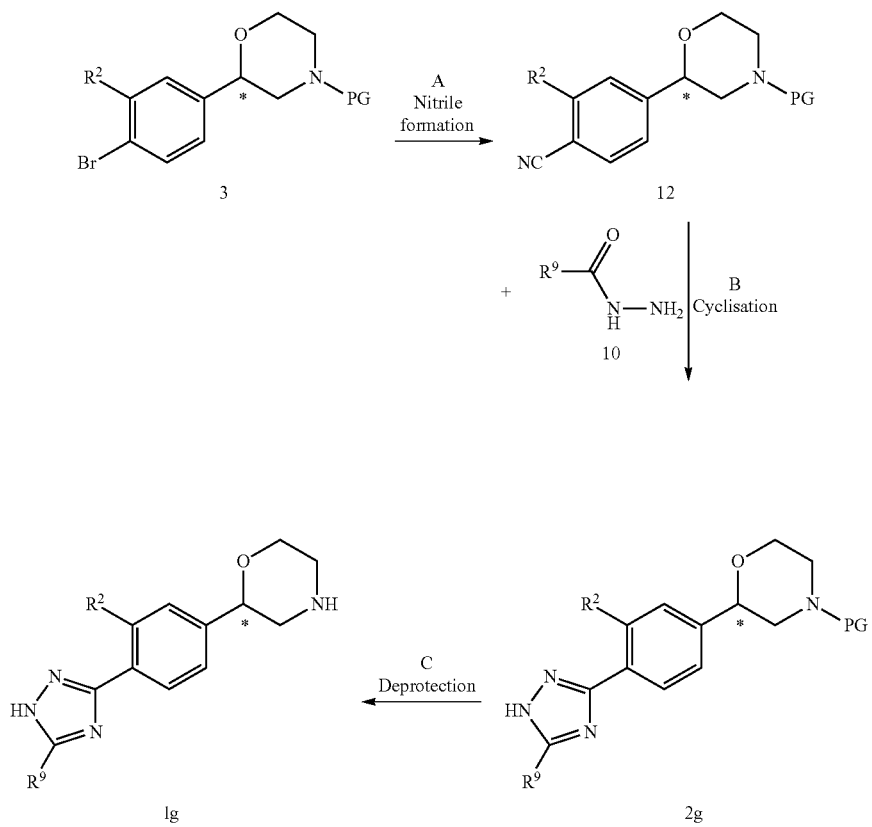

Scheme 7

* Stereochemistry can be R or S or racemic

Scheme 8

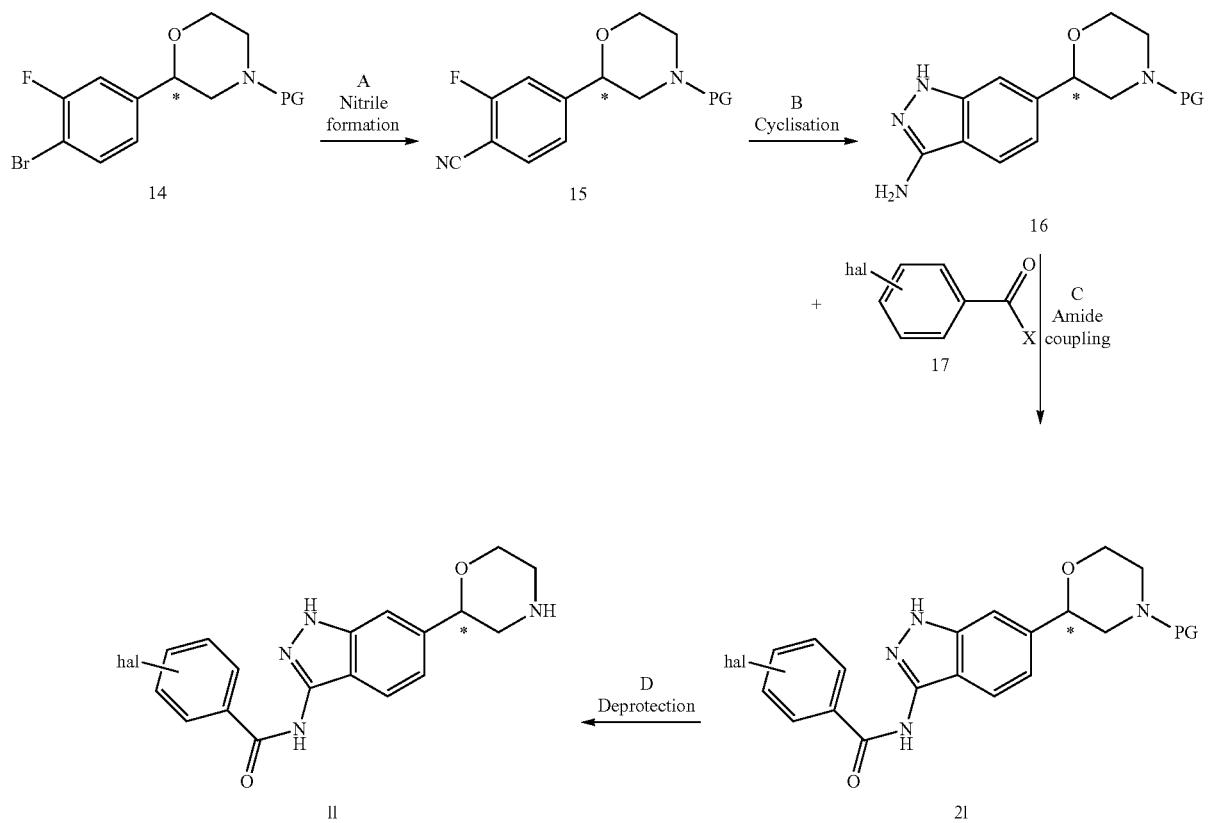

\* Stereochemistry can be R or S or racemic
X = Cl, OH

Step A: Nitrile formation can be accomplished by reaction of dihalogen compound 14 with a suitable reagent such as zinc zyanide and a catalyst such as or tetrakis(triphenylphosphine)palladium(0) in a solvent such as dimethylformamide at temperatures from 20° C.-120° C. for 1 h-24 hrs.

Preferred conditions are the use of zinc zyanide and tetrakis(triphenylphosphine)palladium(0) in dimethylformamide at 85° C. overnight.

Step B: Formation of the aminoindazole 16 can be achieved by reaction of the nitrile 15 with hydrazine, hydrazine hydrate or a hydrazinium salt such as hydrazinium chloride or hydrazinium sulfate in a suitable solvent such as ethanol, methanol, propanol or butan-1-ol with or without a suitable base such as potassium carbonate, sodium carbonate at 20° C. to 140° C. for 1 h to 24 hrs.

Preferred conditions are the use of hydrazinium hydrate in ethanol as solvent at reflux for 18 hrs.

Step C: Amide coupling can be achieved by reaction of aminoindazole 16 with a suitable acylating reagent 17 such as an acid chloride and a base such as diisopropylethylamine, triethylamine or pyridine in a solvent like dichloromethane, dichloroethane, tetrahydrofurane, benzene, toluene, pyridine at temperatures of −20° C. to 100° C. for 1 h to 24 hrs.

Alternatively, an acid can be used as acylating reagent 17 (X=OH) in presence of an amide coupling reagent such as 1-ethyl-3-(3-dimethylaminopropyl)carbodiimide (EDC), dicyclohexylcabodiimde (DCC), O-(Benzotriazol-1-yl)-N,N,N',N'-tetramethyluroniumhexafluoro-phosphate (HBTU), O-(Benzotriazol-1-yl)-N,N,N',N'-tetramethyluroniumtetrafluoroborate (TBTU) or the like and a base such as triethylamine, diisopropylethylamine or pyridine in a solvent such as methylenechloride, 1,2-dichloroethane, tetrahydrofurane or ethyl acetate.

Preferred conditions are the use of an acid chloride in pyridine at room temperature for 18 hrs.

Step D: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 9

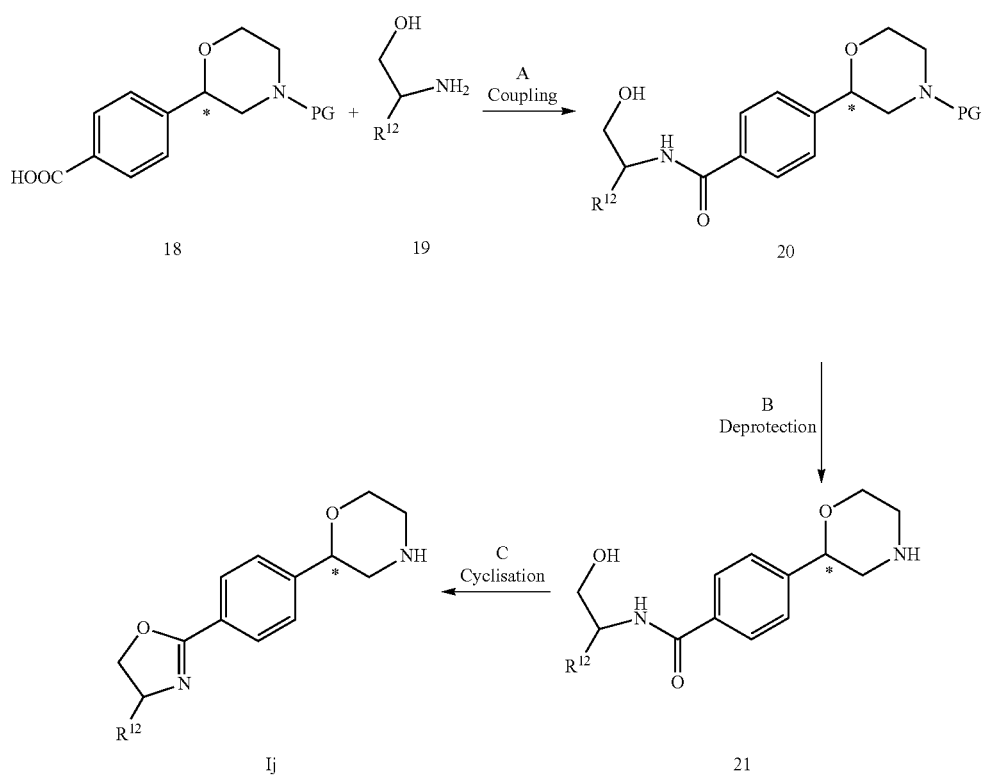

Step A: Amide coupling can be achieved by reaction of acid 18 with an aminoalcohol 19 in presence of a suitable amide coupling reagent such as such as 1-ethyl-3-(3-dimethylaminopropyl)carbodiimide (EDC), dicyclohexylcabodiimde (DCC), O-(Benzotriazol-1-yl)-N,N,N',N'-tetramethyluroniumhexafluorophosphate (HBTU), O-(Benzotriazol-1-yl)-N,N,N',N'-tetramethyluroniumtetrafluoroborate (TBTU) or the like and a base such as triethylamine, diisopropylethylamine, pyridine or dimethylaminopyridine in a solvent such as dichloromethane, 1,2-dichloroethane, tetrahydrofurane or ethyl acetate at −20° C. to 80° C. for 1 h to 24 hrs.

Preferred conditions are the use of 1-ethyl-3-(3-dimethylaminopropyl)carbodiimide (EDC) in dichloromethane at room temperature for 18 hrs.

Step B: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Step C: Cyclisation can be achieved by treatment of intermediate 21 with an activating reagent such as diethylaminosulfur trifluoride (DAST) in dichloromethane at −20° C. to 40° C. for 1 h to 24 hrs.

Preferred conditions are the use of diethylaminosulfur trifluoride (DAST) in dichloromethane for 5 hrs at room temperature.

Scheme 10

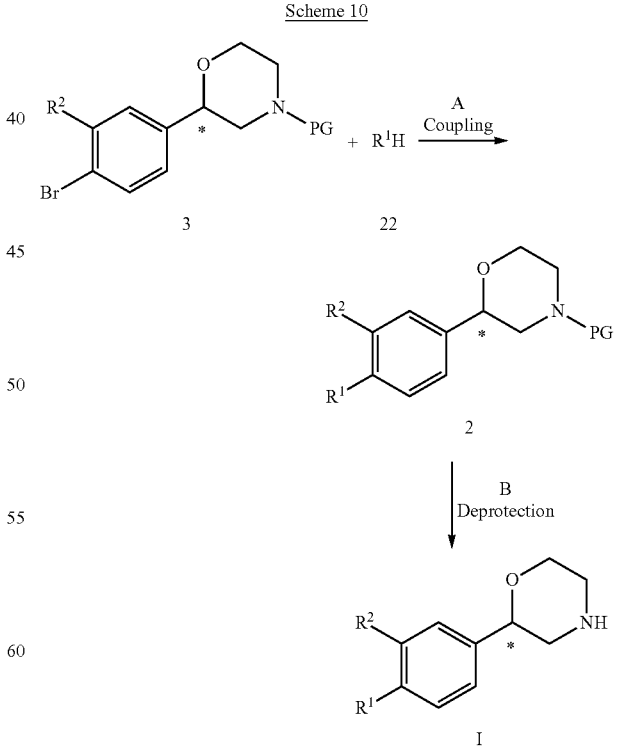

* Stereochemistry can be R or S or racemic

Step A: Coupling of the bromoderivative 3 with a suitable heterocycle 22 can be accomplished by using a copper catalyst such as copper(I)-iodide or copper(I)-bromide in combination with a ligand such as 8-hydroxyquinoline or the like, and a base such as sodium carbonate, potassium carbonate, cesium carbonate in a suitable solvent such as dioxane, dimethylformamide, dimethylacetamide, tetrahydrofurane, dimethoxyetane, diglyme, ethanol, methanol or water or mixtures of these at 20° C. to 180° C. for 15 min to 48 hrs with or without microwave irradiation.

Preferred conditions are the use of copper(I)-iodide, 8-hydroxyquinoline and cesium carbonate in a mixture of dimethylformamide and water at 150° C. for 48 hrs.

Step B: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Step A: Azide formation can be accomplished by reaction of aniline 23a with a suitable reagent such as sodium nitrite and and aqueous acid such as hydrochloric acid or sulfuric acid followed by sodium azide in water at temperature from 0° C. to room temperature for 5 min to 2 hrs.

Preferred conditions are the use of sodium nitrite, hydrochloric acid, sodium azide and water at 0° C. for 20 min.

Step B: Formation of the triazole can be achieved by reaction of the azide 24 with an alkyne 25 in a suitable solvent such as benzene, toluene, dichloromethane, tetrahydrofurane, pyridine, N,N-diisopropylamine or triethylamine with or without a catalyst such as copper salts at −20° C. to 60° C. for 15 min to 18 hrs.

Preferred conditions are the use of copper(I) iodide in N,N-diisopropylamine as solvent at room temperature for 2 hrs.

Step C: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 11

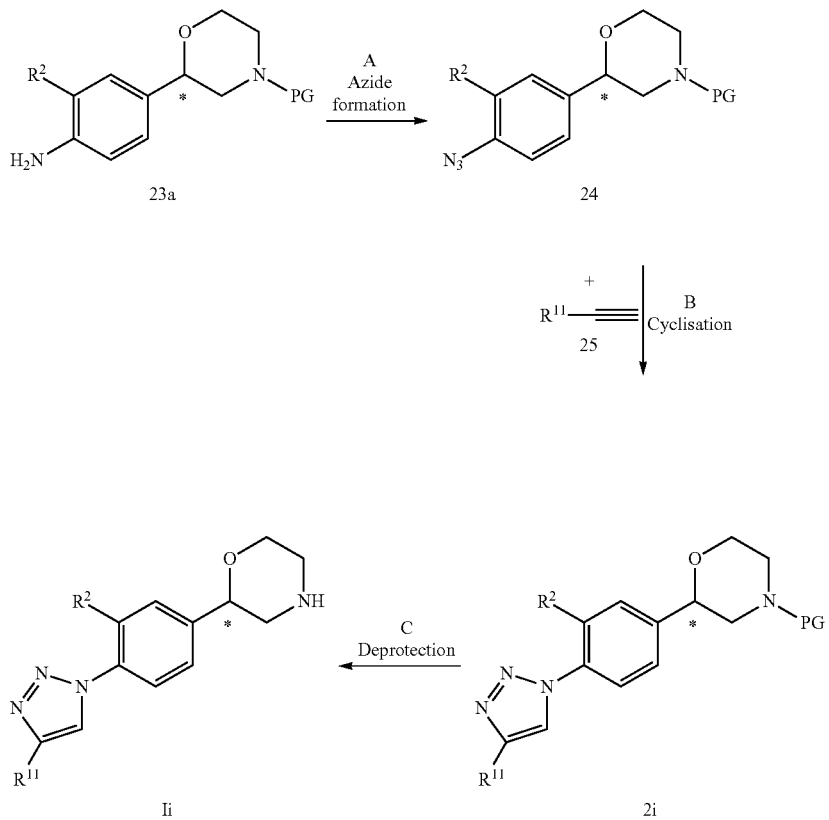

* Stereochemistry can be
R or S or racemic

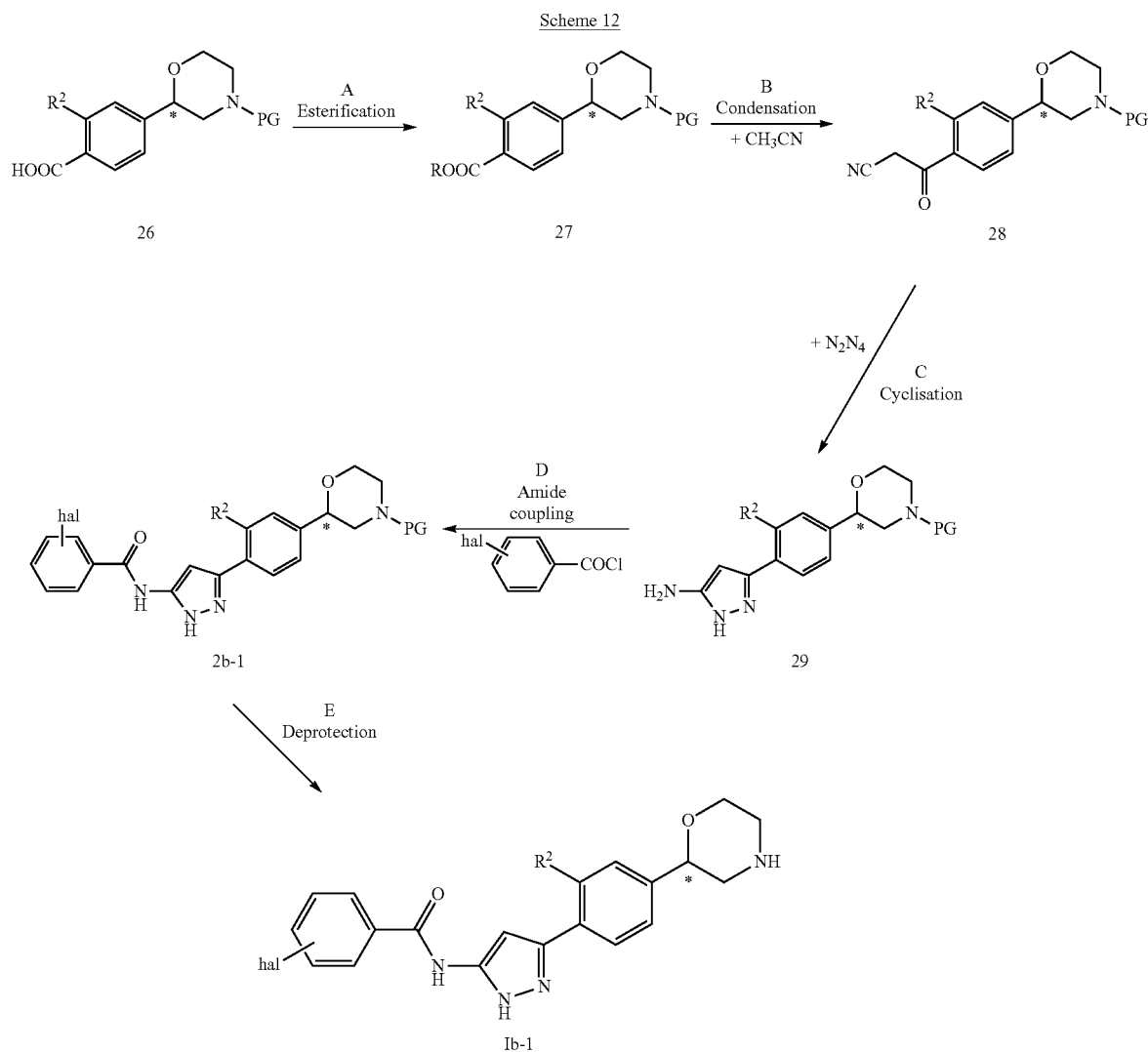

\* Stereochemistry can be R or S or racemic

R = methyl

Step A: Esterification can be accomplished by a variety of methods such as reaction with an alkylhalide in presence of a suitable base such as potassium carbonate, sodium carbonate or cesium carbonate in a solvent such as dimethylformamide, dimethylacetamide or tetrahydrofurane at temperatures from 0° C. to 160° C. for 20 min to 24 hrs. Another method is the reaction of the acid with a alkyldiazo compound such as diazomethane at room temperature for several hours.

Preferred R group is methyl, preferred conditions are the use of methyl iodide, potassium carbonate in dimethylformamide at room temperature overnight.

Step B: Reaction of ester 27 with acetonitrile can be achieved by treatment with a base such as n-butyllithium, sec-butyllithium or the like in a solvent such as tetrahydrofurane, dioxane or ether at −78° C. to 20° C. for 15 min to 18 hrs.

Preferred conditions are the use of n-butyl lithium in tetrahydrofurane at −78° C. for 3 hrs.

Step C: The cyanoacetyl compound 28 can be reacted with hydrazine or its hydrate in a suitable solvent such as ethanol, methanol n-propanol or isopropanol at 0 to 80° C. for 1-18 hrs.

Preferred conditions are reaction with hydrazine hydrate in ethanol at 60° C. for 6 hrs.

Step D: Amide coupling can be achieved by reaction of aminopyrazole 29 with a suitable acylating reagent 4-hal-phenyl-CO—Cl, and a base such as diisopropylethylamine, triethylamine, pyridine or 4-dimethylaminopyridine in a solvent like dichloromethane, dichloroethane, tetrahydrofurane, benzene, toluene, pyridine or a mixture of these at temperatures of −20° C. to 100° C. for 1 h to 24 h.

Alternatively, an acid can be used as acylating reagent 4-hal-phenyl-CO—Cl in presence of an amide coupling reagent such as 1-ethyl-3-(3-dimethylaminopropyl)carbodiimide (EDC), dicyclohexylcabodiimde (DCC), O-(Benzotriazol-1-yl)-N,N,N',N'-tetramethyluroniumhexafluorophosphate (HBTU), O-(Benzotriazol-1-yl)-N,N,N',N'-tetramethyluroniumtetrafluoroborate (TBTU) or the like and a base such as triethylamine, diisopropylethylamine or pyridine in a solvent such as methylenechloride, 1,2-dichloroethane, tetrahydrofurane or ethyl acetate.

Preferred conditions are the use of an acid chloride, pyridine and a catalytic amount of 4-dimethylaminopyridine in a mixture of tetrahydrofurane and dichloromethane at room temperature for 18 hrs.

Step E: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 13

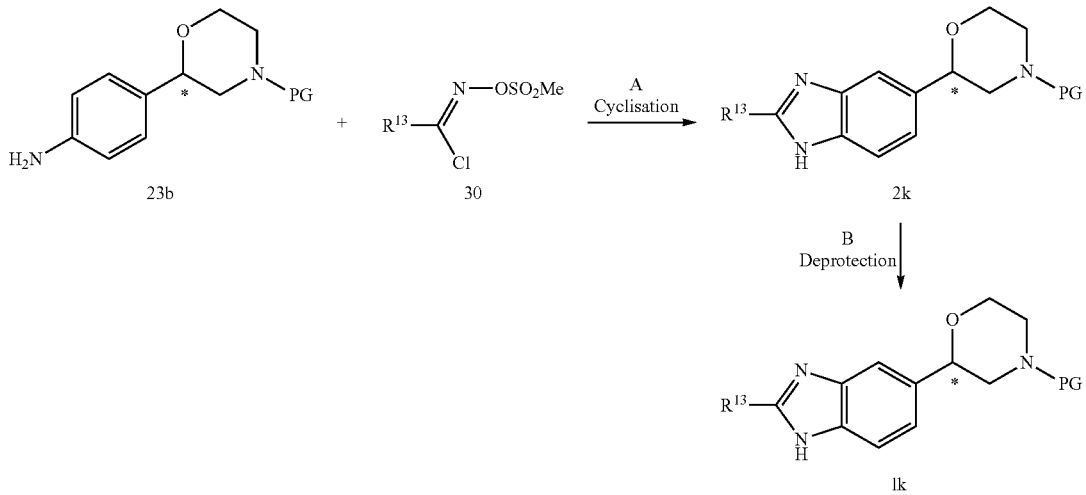

* Stereochemistry can be R or S or racemic

Step A: Cyclisation can be achieved by reaction of the aniline 23b with a methylsulfonyloxy-imidoyl chloride 30 and a suitable base such as N,N,N',N'-tetramethylethylenediamine, triethylamine or dimethylethylamine in a solvent like tetrahydrofurane, toluene, dimethylformamide, chloroform or acetonitrile according to a procedure described for related compounds in Yamamoto et al. (J. Org. Chem 2009, 74, 1394) at temperature from 20° C. to 60° C. for 1 to 24 hrs.

Preferred conditions are the use of N,N,N',N'-tetramethylethylenediamine in tetahydrofurane at 60° C. for 18 hrs.

Step B: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 14

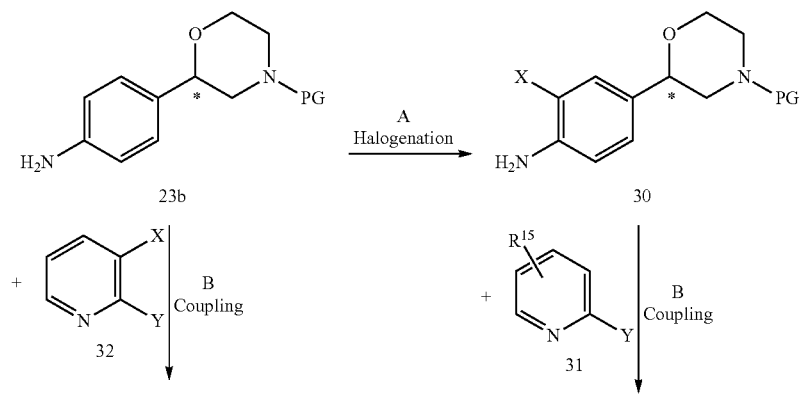

-continued

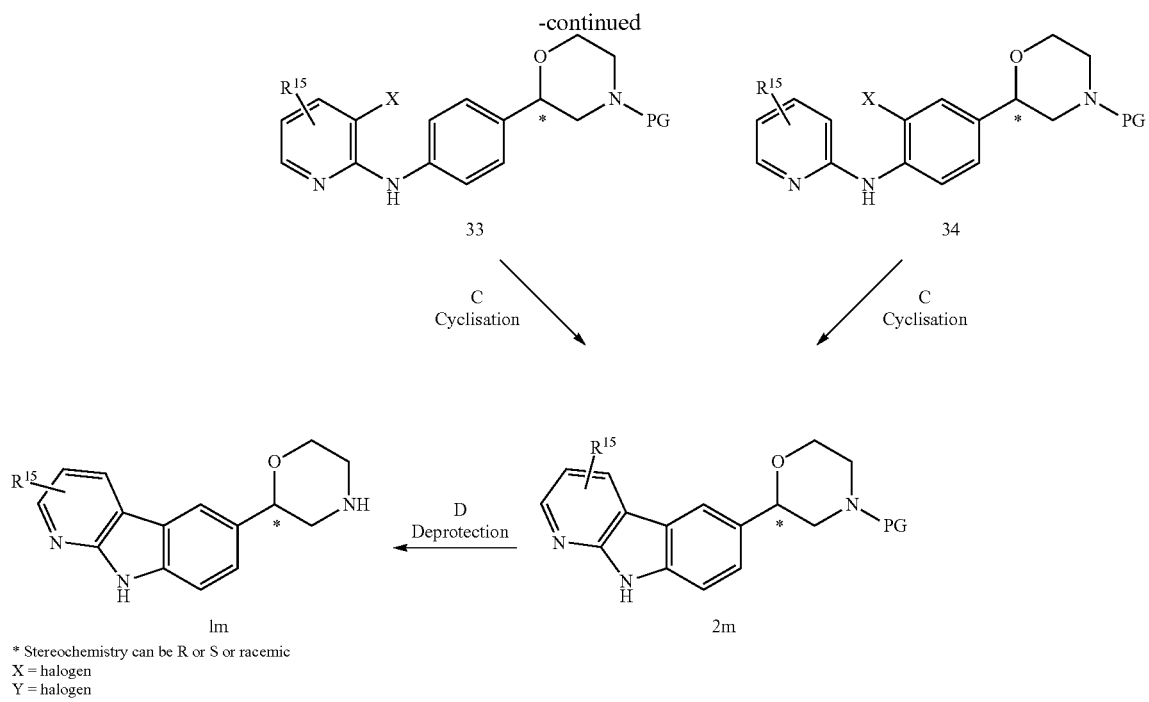

* Stereochemistry can be R or S or racemic
X = halogen
Y = halogen

Step A: Halogenation of the aniline 23b can be accomplished by reaction with a suitable halogenation reagent such as N-chlorosuccinimide or N-bromosuccinimide in tetrachloromethane, chloroform or dimethylformamide at temperature from 0° C. to 75° C. for 15 min to 6 hrs.

Preferred conditions are the use of N-chlorosuccinimide in dimethylformamide at 60° C. for 1 h.

Step B: Coupling of the aniline 23b or the aniline 30 with the pyridine compounds 32 or 31 can be achieved by using a palladium catalyst such as tris(dibenzylideneacetone)dipalladium) or tetrakis(triphenylphosphine)palladium(0) in combination with a ligand suitable ligand such as xanthphos, triphenylphosphine, tricyclohexylphosphine or the like, and a base such as potassium phosphate, potassium carbonate, cesium carbonate in a suitable solvent such as dioxane, dimethylacetamide, dimethylformamide, tetrahydrofurane, dimethoxyethane or diglyme at 50° C. to 140° C. for 1 h to 18 hrs with or without microwave irradiation.

Preferred conditions are the use of tris(dibenzylideneacetone)dipalladium) and cesium carbonate in dioxane at 100° C. for 2 hrs.

Step C: Cyclisation can be achieved by using a palladium catalyst such as palladium(II)-acetate or palladium(II)-chloride with a ligand suitable ligand such triphenylphosphine, tricyclohexylphosphine or the like, and 1,8-diazabicyclo [5.4.0]undec-7-ene in a suitable solvent such as o-xylene or a mixture of o-xylene with dimethylacetamide at 140° C. to 170° C. for 1 h to 18 hrs with or without microwave irradiation.

Preferred conditions are the use of palladium(II)-acetate, tricyclohexylphosphine and 1,8-diazabicyclo[5.4.0]undec-7-ene in a mixture of o-xylene and dimethylacetamide at 155° C. for 16 hrs.

Step D: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 15

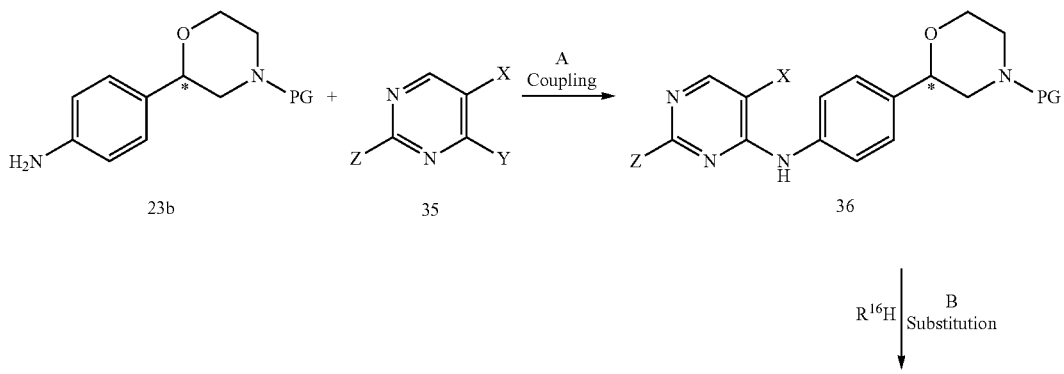

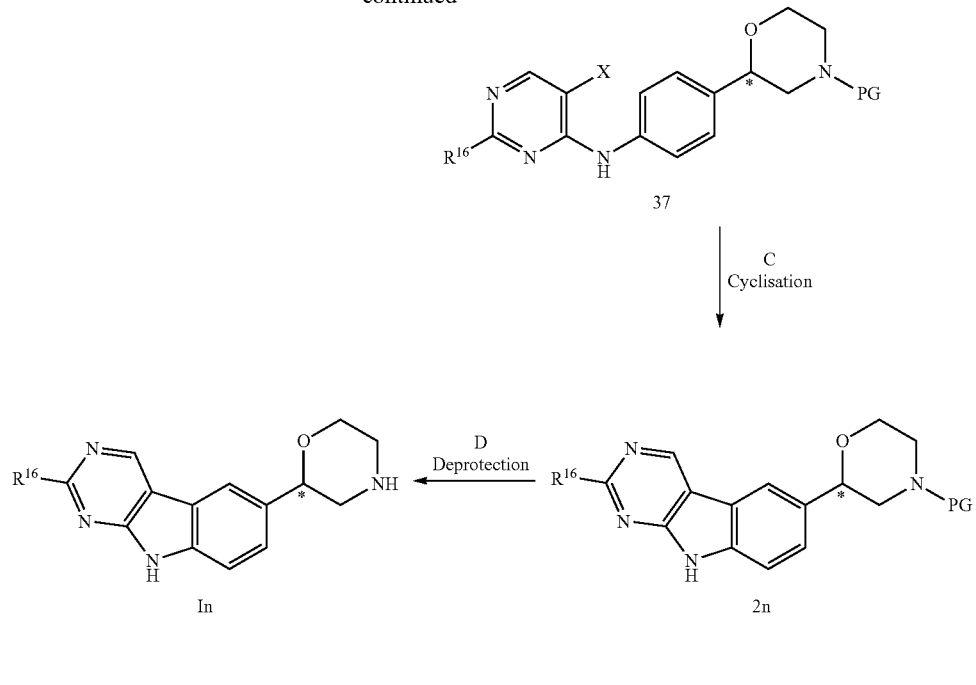

* Stereochemistry can be R or S or racemic

X, Y, Z = Halogen

Step A: Coupling of the aniline 23b with the pyrimidine compound 35 can be achieved by using a palladium catalyst such as tris(dibenzylideneacetone)dipalladium) or tetrakis(triphenylphosphine)palladium(0) in combination with a ligand suitable ligand such as xanthphos, triphenylphosphine, tricyclohexylphosphine or the like, and a base such as potassium phosphate, potassium carbonate, cesium carbonate in a suitable solvent such as dioxane, dimethylacetamide, dimethylformamide, tetrahydrofurane, dimethoxyethane or diglyme at 50° C. to 140° C. for 1 h to 18 hrs with or without microwave irradiation.

Preferred conditions are the use of tris(dibenzylideneacetone)dipalladium) and cesium carbonate in dioxane at 100° C. for 2 hrs.

Step B: Substitution of halogen Z by an alkoxy group $R^{16}$ can be achieved by heating compound 36 with the corresponding alkohol $R^{16}H$ and a base such as potasssium tert-butoxide or sodium hydride or the like at 20° C. to 140° C. for 1 h to 18 hrs.

Preferred conditions are the use of an alkohol together with potassium tert-butoxide at 90° C. overnight.

Step C: Cyclisation can be achieved by using a palladium catalyst such as palladium(II)-acetate or palladium(II)-chloride with a ligand suitable ligand such triphenylphosphine, tricyclohexylphosphine or the like, and 1,8-diazabicyclo[5.4.0]undec-7-ene in a suitable solvent such as o-xylene or a mixture of o-xylene with dimethylacetamide at 140° C. to 170° C. for 1 h to 18 hrs with or without microwave irradiation.

Preferred conditions are the use of palladium(II)-acetate, tricyclohexylphosphine and 1,8-diazabicyclo[5.4.0]undec-7-ene in a mixture of o-xylene and dimethylacetamide at 155° C. for 16 hrs.

Step D: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Scheme 16

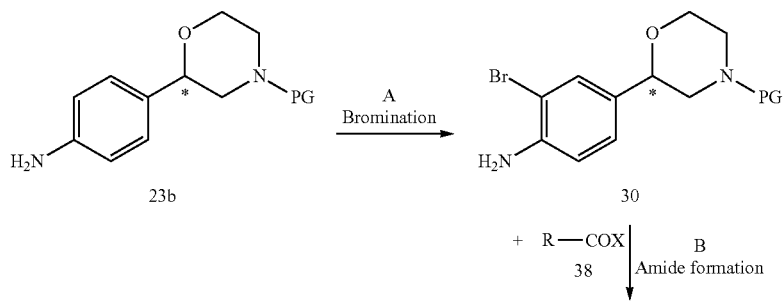

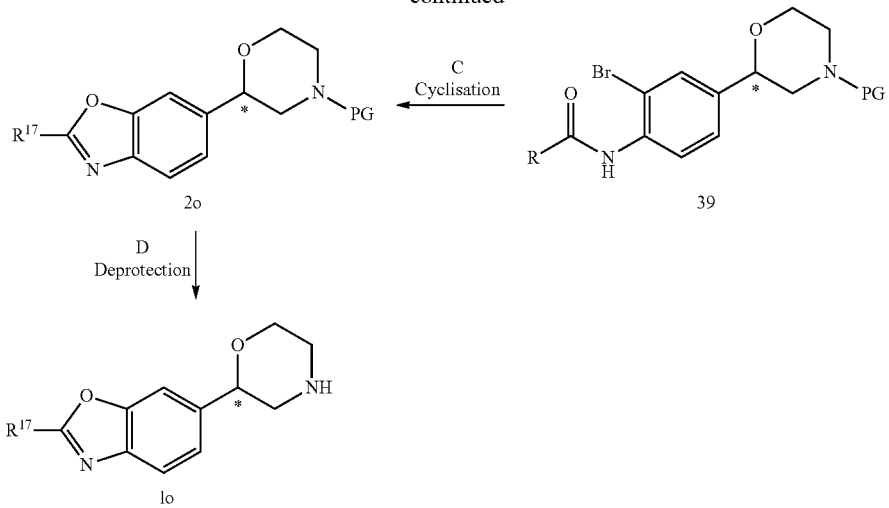

* Stereochemistry can be R or S racemic

Step A: Bromination of the aniline 30 can be accomplished by reaction with a suitable bromination reagent such as N-bromosuccinimide in tetrachloromethane, chloroform or dimethylformamide at temperature from 0° C. to 75° C. for 15 min to 6 hrs.

Preferred conditions are the use of N-bromosuccinimide in dimethylformamide at room temperature for 1 h.

Step B: Amide coupling can be achieved by reaction of bromoaniline 30 with a suitable acylating reagent 38 such as an acid chloride and a base such as diisopropylethylamine, triethylamine or pyridine in a solvent like dichloromethane, dichloroethane, tetrahydrofurane, benzene, toluene, pyridine at temperatures of −20° C. to 100° C. for 1 h to 24 hrs. The acid chloride can be formed from the acid by several methods known in the art, such as treatment of the acide with thionylchloride, phosphoroxychloride, phosphorpentachloride or 1-chloro-N,N2-trimethylpropenylamine with or without an organic solvent.

Alternatively, an acid can be used as acylating reagent in presence of an amide coupling reagent such as 1-ethyl-3-(3-dimethylaminopropyl)carbodiimide (EDC), dicyclohexylcarbodiimde (DCC), O-(Benzotriazol-1-yl)-N,N,N',N'-tetramethyluroniumhexafluoro-phosphate (HBTU), O-(Benzotriazol-1-yl)-N,N,N',N'-tetramethyluroniumtetrafluoroborate (TBTU) or the like and a base such as triethylamine, diisopropylethylamine or pyridine in a solvent such as methylenechloride, 1,2-dichloroethane, tetrahydrofurane or ethyl acetate.

Preferred conditions are the use of an acid chloride, which was freshly prepared from the acid and N,N2-trimethylpropenylamine, and its reaction with the bromoaniline 30 in dichloromethane in the presence of diisopropylethylamine.

Step C: Cyclisation can be achieved by using a copper catalyst such as copper(I)-iodide or copper(I)-triflate with a ligand suitable ligand such 1,10-phenanthroline and a base such as cesium carbonate, sodium carbonate or potassium carbonate in a suitable solvent such as 1,2-dimethoxyethane, 1,4-dioxane or dimethylacetamide at 80° C. to 150° C. for 1 h to 18 hrs.

Preferred conditions are the use of copper(I)-iodide, 1,10-phenathroline and cesium carbonate in 1,2-dimethoxyethane at 125° C. for 18 hrs.

Step D: Cleavage of the amino protecting group can be effected with a variety of methods known in the art. The tert-butoxycarbonyl group can be cleaved using a mineral acid such as HCl, $H_2SO_4$ or $H_3PO_4$ or a organic acid such as $CF_3COOH$, $CHCl_2COOH$, HOAc or p-toluonesulfonic acid in a solvent such as $CH_2Cl_2$, $CHCl_3$, THF, MeOH, EtOH or $H_2O$ at 0 to 60° C.

Preferred conditions are the use of HCl in dioxane for 2 hrs at 60° C. or the use of $CF_3COOH$ in dichloromethane at room temperature overnight.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

V. Examples

Example 1

2-(4-(1H-Benzo[d]imidazol-2-yl)phenyl)morpholine hydrochloride

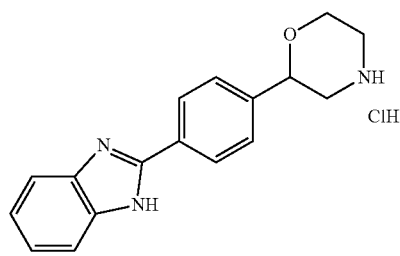 [SMILES: c1ccc2[nH]c(-c3ccc(C4CNCCO4)cc3)nc2c1 ; Cl]

a) tert-Butyl 2-(4-formylphenyl)morpholine-4-carboxylate tert-Butyl 2-(4-bromophenyl)morpholine-4-carboxylate (684 mg, 2 mmol, CAS 1131220-82-0) in THF (6 ml) was cooled to −78° C., treated dropwise with n-butyllithium (1.88 ml, 3 mmol, 1.6 M solution in hexane) and stirred 30 min at −78° C. Dimethylformamide (1 ml, 2 mmol) was added dropwise and the mixture was stirred for 2 h at −78° C., and then allowed to warm up to −10° C. The reaction mixture was quenched by addition of saturated ammonium chloride solution (4 ml) and water (4 ml) and the resulting mixture was partitioned between water and ethyl acetate.

The organic layer was washed with brine, dried over MgSO4 and concentrated in vacuo. The residue was purified by flash chromatography (20 g silica gel, heptane/ethyl acetate 4:1) yielding 320 mg of an off-white solid. MS (ISP): 292.3 ([M+H]$^+$).

b) tert-Butyl 2-(4-(1H-benzo[d]imidazol-2-yl)phenyl)morpholine-4-carboxylate tert-Butyl 2-(4-formylphenyl)morpholine-4-carboxylate (300 mg, 1.03 mmol) was dissolved in dimethylacetamide (4.5 ml). 1,2-Diaminobenzene (134 mg, 1.24 mmol) and sodium metabisulfite (294 mg, 1.54 mmol) were added and the reaction mixture was stirred at 90° C. overnight. After cooling, the reaction mixture was poured into water and extracted with ethyl acetate. The organic layer was dried over MgSO4 and evaporated. The crude material was purified by flash chromatography (20 g silica gel, 40 to 70% ethyl acetate in heptane) to yield a white solid (333 mg, 85%). MS (ISP): 280.3 (100%, [M-BOC+H]$^+$), 380.2 (20%, [M+H]$^+$).

c) 2-(4-(1H-Benzo[d]imidazol-2-yl)phenyl)morpholine hydrochloride tert-Butyl 2-(4-(1H-benzo[d]imidazol-2-yl)phenyl)morpholine-4-carboxylate (330 mg, 0.87 mmol) was dissolved in dioxane (12 ml) and a solution of HCl in dioxane (4M, 3.25 ml, 13 mmol) was added. The reaction mixture was stirred overnight at room temperature. The solid was filtered off, washed with ether and dried in vacuo at 60° C. to afford 2-(4-(1H-benzo[d]imidazol-2-yl)phenyl)morpholine hydrochloride (232 mg, 85%) as an off-white solid. MS (ISP): 280.1 ([M+H]$^+$).

Example 2

2-(4-(6-Chloro-1H-benzo[d]imidazol-2-yl)phenyl)morpholine hydrochloride

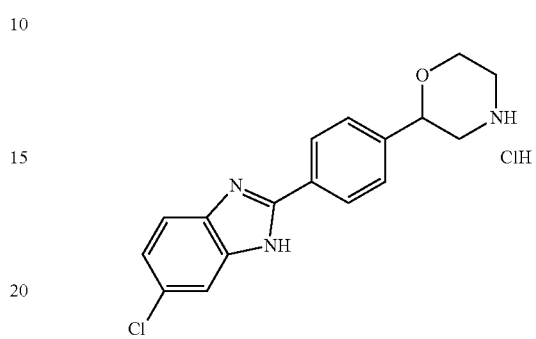

The title compound was obtained in analogy to example 1 using 4-chloro-1,2-diaminobenzene instead of 1,2-diaminobenzene in step b). Off-white solid. MS (ISP): 313.9 ([{$^{35}$Cl}M+H]$^+$), 315.2 ([{$^{37}$Cl}M+H]$^+$).

Example 3

2-(4-(5-(4-Chlorophenyl)-1H-pyrazol-3-yl)phenyl)morpholine hydrochloride

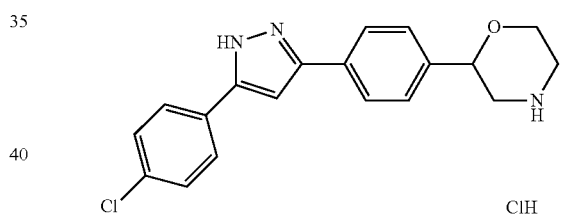

a) tert-Butyl 2-(4-acetylphenyl)morpholine-4-carboxylate tert-Butyl 2-(4-bromophenyl)morpholine-4-carboxylate (750 mg, 2.19 mmol, CAS 1131220-82-0) in THF (6 ml) was cooled to −78° C., treated dropwise with n-butyllithium (2.05 ml, 3.29 mmol, 1.6 M solution in hexane) and stirred 1 h at −78° C. N-Methoxy-N-methylacetamide (226 mg, 2.19 mmol) was added and the mixture was stirred for 1 h at −78° C., and then allowed to warm up to −5° C. The reaction mixture was quenched by addition of saturated ammonium chloride solution (4 ml) and water (4 ml) and the resulting mixture was partitioned between water and ethyl acetate.

The organic layer was washed with brine, dried over MgSO4 and concentrated in vacuo. The residue was purified by flash chromatography (20 g silica gel, heptane/ethyl acetate 4:1) yielding 430 mg of a white solid. MS (ISP): 323.3 ([M+NH$_4$]$^+$).

b) tert-Butyl 2-(4-(3-(4-chlorophenyl)-3-oxopropanoyl)phenyl)morpholine-4-carboxylate tert-Butyl 2-(4-acetylphenyl)morpholine-4-carboxylate (210 mg, 0.69 mmol) was dissolved in THF (3.5 ml).

Lithium-bis-(trimethylsilyl)-amide solution (2.05 ml, 2.05 mmol, 1.0 M solution in THF) was added dropwise and the yellow reaction mixture was stirred at −78° C. for 1 hour. 4-Chlorobenzoyl chloride (120 mg, 0.69 mmol) was added and the reaction mixture was stirred for 90 min and was quenched by addition of 1M aqueous hydrochloric acid. Ethyl acetate was added and the organic layer was dried over MgSO4 and evaporated. The crude material was purified by flash chromatography (10 g silica gel, 10 to 50% ethyl acetate in heptane) to yield an off-white solid (215 mg, 70%). MS (ISP): 388.2 ([{$^{35}$Cl}M-$^t$Bu+H]$^+$), 390.3 ([{$^{37}$Cl}M-$^t$Bu+H]$^+$).

c) tert-Butyl 2-(4-(5-(4-chlorophenyl)-1H-pyrazol-3-yl)phenyl)morpholine-4-carboxylate A solution of tert-butyl 2-(4-(3-(4-chlorophenyl)-3-oxo-propanoyl)phenyl)morpholine-4-carboxylate (210 mg, 0.473 mmol) and hydrazine hydrate (35.5 mg, 0.70 mmol) in ethanol (3.5 ml) was heated to reflux with stirring overnight. The clear yellow solution was evaporated under reduced pressure, water was added and ethyl acetate. The organic layer was separated, the aqueous layer was extracted again with ethyl acetate. The combined organic layers were dried over MgSO4 and evaporated. The crude material was purified by flash chromatography (10 g silica gel, 10 to 50% ethyl acetate in heptane) to yield a white solid (208 mg, 89%). MS (ISP neg): 438.3 ([{$^{35}$Cl}M−H]$^+$), 440.4 ([{$^{37}$Cl}M−H]$^+$).

d) 2-(4-(5-(4-Chlorophenyl)-1H-pyrazol-3-yl)phenyl)morpholine hydrochloride tert-Butyl 2-(4-(5-(4-chlorophenyl)-1H-pyrazol-3-yl)phenyl)morpholine-4-carboxylate (180 mg, 0.41 mmol) was dissolved in dioxane (5.5 ml) and a solution of HCl in dioxane (4M, 1.53 ml, 6.15 mmol) was added. The reaction mixture was stirred for 2 h at 60° C. and overnight at room temperature. The solid was filtered off, washed with ether and dried in vacuo to afford 2-(4-(5-(4-chlorophenyl)-1H-pyrazol-3-yl)phenyl)morpholine hydrochloride (131 mg, 85%) as a white solid. MS (ISP): 340.1 ([{$^{35}$Cl}M+H]$^+$), 342.1 ([{$^{37}$Cl}M+H]$^+$).

Example 4

2-(4-(5-(4-Fluorophenyl)-1H-pyrazol-3-yl)phenyl)morpholine hydrochloride

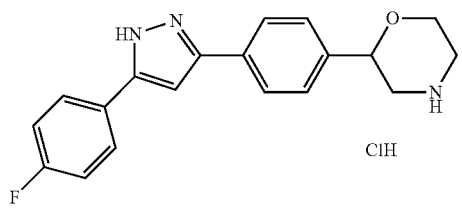 [SMILES: Fc1ccc(-c2cc(-c3ccc(C4CNCCO4)cc3)n[nH]2)cc1 ; Cl]

The title compound was obtained in analogy to example 3 using 4-fluorobenzoyl chloride instead of 4-chlorobenzoyl chloride in step b). White solid. MS (ISP): 324.3 ([M+H]$^+$).

Example 5

2-(4-(5-(6-Chloropyridin-3-yl)-1H-pyrazol-3-yl)phenyl)morpholine hydrochloride

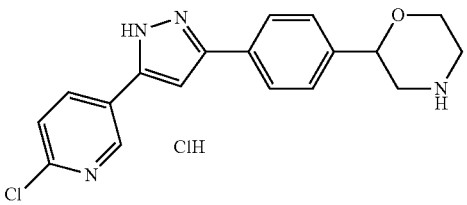 [SMILES: Clc1ccc(-c2cc(-c3ccc(C4CNCCO4)cc3)n[nH]2)cn1 ; Cl]

The title compound was obtained in analogy to example 3 using 6-chloronicotinoyl chloride instead of 4-chlorobenzoyl chloride in step b). White solid. MS (ISP): 341.1 ([M+H]$^+$).

Example 6

4-(3-(4-(Morpholin-2-yl)phenyl)-1H-pyrazol-5-yl)benzonitrile hydrochloride

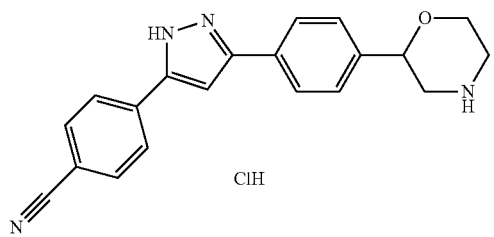 [SMILES: N#Cc1ccc(-c2cc(-c3ccc(C4CNCCO4)cc3)n[nH]2)cc1 ; Cl]

The title compound was obtained in analogy to example 3 using 4-cyanobenzoyl chloride instead of 4-chlorobenzoyl chloride in step b). White solid. MS (ISP): 331.1 ([M+H]$^+$).

Example 7

(S)-2-(4-(6-bromo-1H-imidazo[4,5-b]pyridin-2-yl)phenyl)morpholine hydrochloride

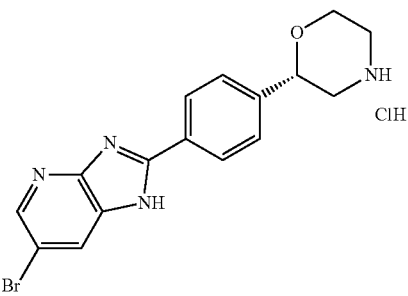

The title compound was obtained in analogy to example 1 using (S)-tert-butyl 2-(4-formylphenyl)morpholine-4-carboxylate instead of tert-butyl 2-(4-formylphenyl)morpholine-4-carboxylate and 3-bromopyridine-1,2-diamine instead of 1,2-diaminobenzene in step b). Off-white solid. MS (ISP): 359.1 ([{$^{79}$Br}M+H]$^+$), 361.1 ([{$^{81}$Br}M+H]$^+$).

Example 8

(R)-2-(4-(5-(3-Chlorophenyl)-1H-pyrazol-3-yl)phenyl)morpholine hydrochloride

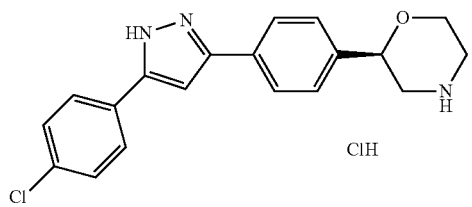 [SMILES: Clc1ccc(-c2cc(-c3ccc([C@@H]4CNCCO4)cc3)n[nH]2)cc1 ; Cl]

a) tert-Butyl 2-(4-(5-(3-chlorophenyl)-1H-pyrazol-3-yl)phenyl)morpholine-4-carboxylate tert-Butyl 2-(4-(5-(3-chlorophenyl)-1H-pyrazol-3-yl)phenyl)morpholine-4-carboxylate was obtained in analogy to example 3 using 3-chlorobenzoyl chloride instead of 4-chlorobenzoyl chloride in step b). White solid. MS (ISP neg): 438.3 ([$\{^{35}Cl\}$M–H]$^+$), 440.4 ([$\{^{37}Cl\}$M–H]$^+$).

b) (R)-tert-Butyl 2-(4-(5-(3-chlorophenyl)-1H-pyrazol-3-yl)phenyl)morpholine-4-carboxylate (R)-tert-Butyl 2-(4-(5-(3-chlorophenyl)-1H-pyrazol-3-yl)phenyl)morpholine-4-carboxylate was obtained by chromatographic separation of the enantiomers. By separation of 159 mg of tert-butyl 2-(4-(5-(3-chlorophenyl)-1H-pyrazol-3-yl)phenyl)morpholine-4-carboxylate on a Chiralpak AD column (eluent heptane/ethanol) 52 mg of (R)-tert-butyl 2-(4-(5-(3-chlorophenyl)-1H-pyrazol-3-yl)phenyl)morpholine-4-carboxylate and 52 mg of the (S)-enantiomer were obtained. White solid. MS (ISP): 440.2 ([$\{^{35}Cl\}$M+H]$^+$), 442.2 ([$\{^{37}Cl\}$M+H]$^+$).

c) (R)-2-(4-(5-(3-Chlorophenyl)-1H-pyrazol-3-yl)phenyl)morpholine hydrochloride The title compound was obtained in analogy to example 3 using (R)-tert-butyl 2-(4-(5-(3-chlorophenyl)-1H-pyrazol-3-yl)phenyl)morpholine-4-carboxylate instead of tert-butyl 2-(4-(3-(4-chlorophenyl)-3-oxopropanoyl)phenyl)morpholine-4-carboxylate in step d). White solid. MS (ISP): 340.1 ([$\{^{35}Cl\}$M+H]$^+$), 342.1 ([$\{^{37}Cl\}$M+H]$^+$).

Example 9

(S)-2-(4-(5-(3-Chlorophenyl)-1H-pyrazol-3-yl)phenyl)morpholine hydrochloride

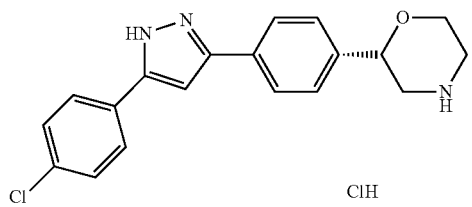

a) tert-Butyl 2-(4-(5-(3-chlorophenyl)-1H-pyrazol-3-yl)phenyl)morpholine-4-carboxylate tert-Butyl 2-(4-(5-(3-chlorophenyl)-1H-pyrazol-3-yl)phenyl)morpholine-4-carboxylate was obtained in analogy to example 3 using 3-chlorobenzoyl chloride instead of 4-chlorobenzoyl chloride in step b). White solid. MS (ISP neg): 438.3 ([$\{^{35}Cl\}$M–H]$^+$), 440.4 ([$\{^{37}Cl\}$M–H]$^+$).

b) (S)-tert-Butyl 2-(4-(5-(3-chlorophenyl)-1H-pyrazol-3-yl)phenyl)morpholine-4-carboxylate (S)-tert-Butyl 2-(4-(5-(3-chlorophenyl)-1H-pyrazol-3-yl)phenyl)morpholine-4-carboxylate was obtained by chromatographic separation of the enantiomers. By separation of 159 mg of tert-butyl 2-(4-(5-(3-chlorophenyl)-1H-pyrazol-3-yl)phenyl)morpholine-4-carboxylate on a Chiralpak AD column (eluent heptane/ethanol) 52 mg of (S)-tert-butyl 2-(4-(5-(3-chlorophenyl)-1H-pyrazol-3-yl)phenyl)morpholine-4-carboxylate and 52 mg of the (R)-enantiomer was obtained. White solid. MS (ISP): 440.2 ([$\{^{35}Cl\}$M+H]$^+$), 442.2 ([$\{^{37}Cl\}$M+H]$^+$).

c) (S)-2-(4-(5-(3-Chlorophenyl)-1H-pyrazol-3-yl)phenyl)morpholine hydrochloride The title compound was obtained in analogy to example 3 using (S)-tert-butyl 2-(4-(5-(3-chlorophenyl)-1H-pyrazol-3-yl)phenyl)morpholine-4-carboxylate instead of tert-butyl 2-(4-(3-(4-chlorophenyl)-3-oxopropanoyl)phenyl)morpholine-4-carboxylate in step d). White solid. MS (ISP): 340.1 ([$\{^{35}Cl\}$M+H]$^+$), 342.1 ([$\{^{37}Cl\}$M+H]$^+$).

Example 10

(S)-2-(4-(6-Fluoro-1H-benzo[d]imidazol-2-yl)phenyl)morpholine hydrochloride

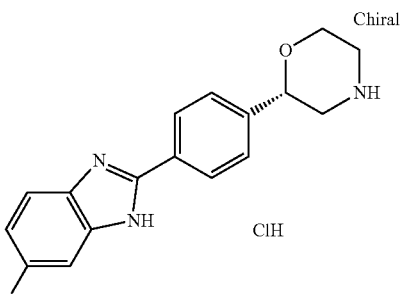

The title compound was obtained in analogy to example 1 using (S)-tert-butyl 2-(4-formylphenyl)morpholine-4-carboxylate instead of tert-butyl 2-(4-formylphenyl)morpholine-4-carboxylate and 1,2-diamino-4-fluoro-diaminobenzene instead of 1,2-diaminobenzene in step b). Light-brown solid. MS (ISP): 298.2 ([M+H]⁺).

Example 11

(S)-2-(4-(4,6-Difluoro-1H-benzo[d]imidazol-2-yl)phenyl)morpholine hydrochloride

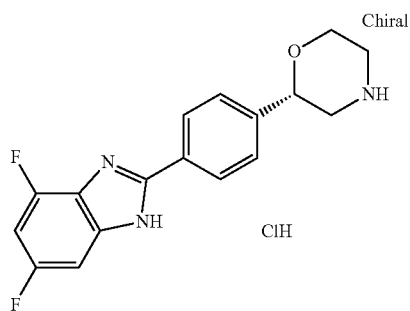

The title compound was obtained in analogy to example 1 using (S)-tert-butyl 2-(4-formylphenyl)morpholine-4-carboxylate instead of tert-butyl 2-(4-formylphenyl)morpholine-4-carboxylate and 1,2-diamino-3,5-difluoro-diaminobenzene instead of 1,2-diaminobenzene in step b). Light-yellow solid. MS (ISP): 316.1 ([M+H]⁺).

Example 12

3-[5-(4-Morpholin-2-yl-phenyl)-2H-pyrazol-3-yl]-benzonitrile hydrochloride

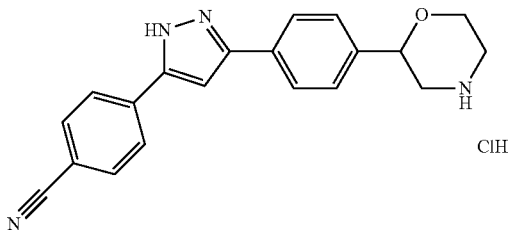 [SMILES: N#Cc1ccc(-c2cc(-c3ccc(C4CNCCO4)cc3)n[nH]2)cc1 ; Cl]

The title compound was obtained in analogy to example 3 using 3-cyanobenzoyl chloride instead of 4-chlorobenzoyl chloride in step b). Off-white solid. MS (ISP): 331.1 ([M+H]⁺).

Example 13

(S)-2-(4-(5-(2,4-Difluorophenyl)-1H-pyrazol-3-yl)phenyl)morpholine hydrochloride

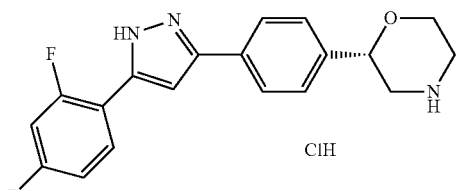

The title compound was obtained in analogy to example 3 using (S)-tert-butyl 2-(4-bromophenyl)morpholine-4-carboxylate instead of tert-butyl 2-(4-bromophenyl)morpholine-4-carboxylate in step a) and 2,4-difluorobenzoyl chloride instead of 4-chlorobenzoyl chloride in step b). Light-yellow solid. MS (ISP): 342.1 ([M+H]⁺).

Example 14

(R)-2-(4-(5-(2,4-Difluorophenyl)-1H-pyrazol-3-yl)phenyl)morpholine hydrochloride

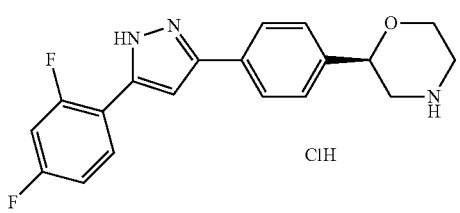 [SMILES: Fc1ccc(-c2cc(-c3ccc([C@@H]4CNCCO4)cc3)n[nH]2)c(F)c1 ; Cl]

The title compound was obtained in analogy to example 3 using (R)-tert-butyl 2-(4-bromophenyl)morpholine-4-carboxylate instead of tert-butyl 2-(4-bromophenyl)morpholine-4-carboxylate in step a) and 2,4-difluorobenzoyl chloride instead of 4-chlorobenzoyl chloride in step b). Light-yellow solid. MS (ISP): 342.1 ([M+H]⁺).

Example 15

(R)-2-(4-(6-Fluoro-1H-benzo[d]imidazol-2-yl)phenyl)morpholine hydrochloride

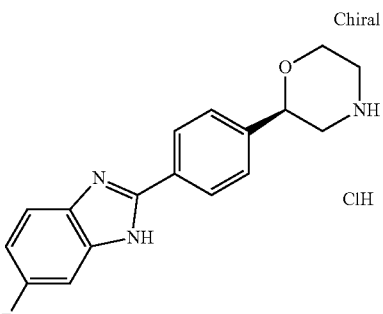

The title compound was obtained in analogy to example 1 using (R)-tert-butyl 2-(4-formylphenyl)morpholine-4-carboxylate instead of tert-butyl 2-(4-formylphenyl)morpholine-4-carboxylate and 1,2-diamino-4-fluoro-diaminobenzene instead of 1,2-diaminobenzene in step b). Light-red solid. MS (ISP): 298.2 ([M+H]⁺).

Example 16

(S)-2-(4-(5,6-Dimethyl-1H-benzo[d]imidazol-2-yl)phenyl)morpholine hydrochloride

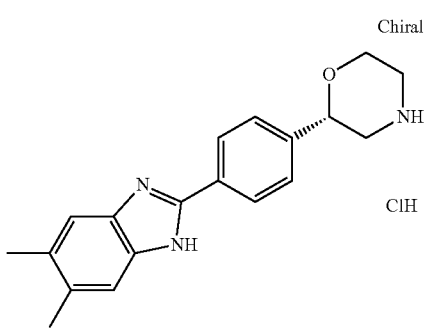 [SMILES: Cc1cc2nc(-c3ccc([C@H]4CNCCO4)cc3)[nH]c2cc1C ; Cl]

The title compound was obtained in analogy to example 1 using (S)-tert-butyl 2-(4-formylphenyl)morpholine-4-carboxylate instead of tert-butyl 2-(4-formylphenyl)morpholine-4-carboxylate and 1,2-diamino-4,5-dimethyl-diaminobenzene instead of 1,2-diaminobenzene in step b). Off-white solid. MS (ISP): 308.3 ([M+H]⁺).

Example 17

(S)-2-(4-(5-(4-Fluorophenyl)-1,3,4-oxadiazol-2-yl)phenyl)morpholine hydrochloride

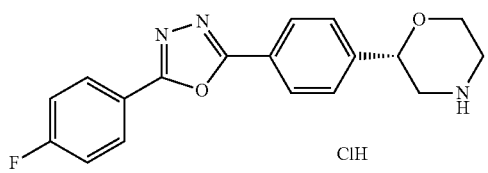 [SMILES: Fc1ccc(-c2nnc(-c3ccc([C@H]4CNCCO4)cc3)o2)cc1 ; Cl]

a) (S)-tert-Butyl 2-(4-((2-(4-fluorobenzoyl)hydrazono)methyl)phenyl)morpholine-4-carboxylate (S)-tert-Butyl 2-(4-formylphenyl)morpholine-4-carboxylate (120 mg, 0.41 mmol) and 4-fluorobenzohydrazide (64 mg, 0.41 mmol) were dissolved in ethanol (2 ml) and stirred for 2 h at room temperature. The solvent was evaporated and ether/ethanol (3:1) was added to precipitate the product. The crystals were filtered off to yield a white solid (101 mg, 58%). MS (ISP): 327.1 ([M-tBu+H]⁺).

b) (S)-tert-Butyl 2-(4-(5-(4-fluorophenyl)-1,3,4-oxadiazol-2-yl)phenyl)morpholine-4-carboxylate

[Bis(trifluoroacetoxy)iodo]benzene (90.5 mg, 0.211 mmol) was dissolved in chloroform (5 ml), then (S)-tert-butyl 2-(4-((2-(4-fluorobenzoyl)hydrazono)methyl)phenyl)morpholine-4-carboxylate (75 mg, 0.175 mmol) was added and the mixture was stirred at room temperature for 20 min. The solvent was evaporated and the residue was purified by flash chromatography (10 g silica gel, 10 to 20% ethyl acetate in heptane) to yield a white solid (49 mg, 66%). MS (ISP): 370.1 ([M-tBu+H]⁺), 426.1 ([M+H]⁺).

c) (S)-2-(4-(5-(4-Fluorophenyl)-1,3,4-oxadiazol-2-yl)phenyl)morpholine hydrochloride (S)-tert-Butyl 2-(4-(5-(4-fluorophenyl)-1,3,4-oxadiazol-2-yl)phenyl)morpholine-4-carboxylate (45 mg, 0.105 mmol) was dissolved in dioxane (1 ml) and a solution of HCl in dioxane (4M, 0.317 ml, 1.27 mmol) was added. The reaction mixture was stirred for 2 h at 60° C. After cooling ether (2 ml) was added and the solid was filtered off. It was washed with ether and dried in vacuo to afford (S)-2-(4-(5-(4-fluorophenyl)-1,3,4-oxadiazol-2-yl)phenyl)morpholine hydrochloride (32 mg, 84%) as a white solid. MS (ISP): 326.1 ([M+H]⁺).

Example 18

(S)-2-(4-(1-(4-Fluorophenyl)-1H-1,2,3-triazol-4-yl)phenyl)morpholine hydrochloride

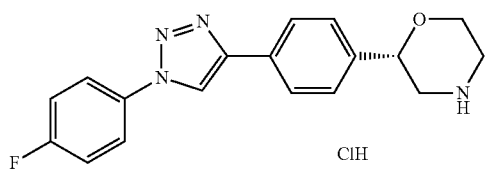 [SMILES: Fc1ccc(-n2cc(-c3ccc([C@H]4CNCCO4)cc3)nn2)cc1 ; Cl]

a) (S)-tert-butyl 2-(4-ethynylphenyl)morpholine-4-carboxylate (S)-tert-Butyl 2-(4-formylphenyl)morpholine-4-carboxylate (120 mg, 0.41 mmol) was dissolved in methanol (5 ml), then potassium carbonate (114 mg, 0.824 mmol) was added, followed by dimethyl 1-diazo-2-oxopropylphosphonate (99 mg, 0.515 mmol). The mixture was stirred for 2 h at room temperature. Ethyl acetate (50 ml) and sodium bicarbonate solution (50 ml) were added, the aqueous phase re-extracted with ethyl acetate. The combined organic layers were dried (MgSO4) and evaporated. The residue was purified by flash chromatography (10 g silica gel, 10 to 20% ethyl acetate in heptane) to yield a colorless oil (103 mg, 87%).

b) (S)-tert-Butyl 2-(4-(1-(4-fluorophenyl)-1H-1,2,3-triazol-4-yl)phenyl)morpholine-4-carboxylate 1-Azido-4-fluorobenzene (24 mg, 0.174 mmol) was dissolved in N,N-diisopropylethylamine (0.75 ml), then (S)-tert-butyl 2-(4-ethynylphenyl)morpholine-4-carboxylate (50 mg, 0.175 mmol) was added followed by copper(I) iodide (33 mg, 0.174 mmol). The mixture was stirred at room temperature for 3 h. The green mixture was concentrated on the rotavap, silica gel (0.5 g) was added and after short grinding the mixture was put on a silica gel column for purification. Flash chromatography (5 g silica gel, 30% ethyl acetate in heptane) yielded a white solid (21 mg, 28%). MS (ISP): 369.1 ([M-tBu+H]⁺), 425.2 ([M+H]⁺).

c) (S)-2-(4-(1-(4-Fluorophenyl)-1H-1,2,3-triazol-4-yl)phenyl)morpholine hydrochloride (S)-tert-Butyl 2-(4-(1-(4-fluorophenyl)-1H-1,2,3-triazol-4-yl)phenyl)morpholine-4-carboxylate (20 mg, 0.047 mmol) was dissolved in dioxane (1 ml) and a solution of HCl in dioxane (4M, 0.14 ml, 0.56 mmol) was added. The reaction mixture was stirred for 2 h at 60° C. After cooling ether (2 ml) was added and the solid was filtered off. It was washed with ether and dried in vacuo to afford (S)-2-(4-(5-(4-fluorophe-

Example 19

(S)-2-(4-(1-(4-Fluorophenyl)-1H-pyrazol-4-yl)phenyl)morpholine hydrochloride

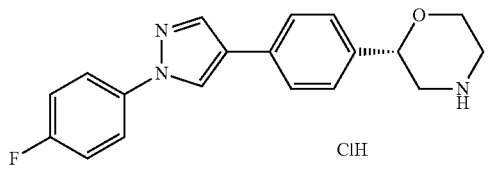 [SMILES: Fc1ccc(-n2cc(-c3ccc([C@H]4CNCCO4)cc3)cn2)cc1 ; Cl]

a) (S)-tert-Butyl 2-(4-(1-(4-fluorophenyl)-1H-pyrazol-4-yl)phenyl)morpholine-4-carboxylate A mixture of (S)-tert-butyl 2-(4-bromophenyl)morpholine-4-carboxylate (100 mg, 0.29 mmol), 1-(4-fluorophenyl)-1H-pyrazole-4-ylboronic acid (60 mg, 0.29 mmol), tribasic potassium phosphate (124 mg, 0.585 mmol) and tetrakis(triphenylphosphine)palladium(0) (13.5 mg, 0.0117 mmol) in dimethylacetamide (2 ml) was placed in a microwave tube, closed and heated at 150° C. for 10 min using a microwave synthesizer (Personal Chemistry Emrys Optimizer). After cooling water (10 ml) was added, and the reaction mixture was extracted with ethyl acetate. The aqueous phase was re-extracted with ethyl acetate twice. The combined organic layers were dried (MgSO4) and evaporated. The residue was purified by flash chromatography (12 g silica gel, 10 to 50% ethyl acetate in heptane) to yield a light brown solid (45 mg, 36%). MS (ISP): 424.1 ([M+H]$^+$).

b) (S)-2-(4-(1-(4-Fluorophenyl)-1H-pyrazol-4-yl)phenyl)morpholine hydrochloride (S)-tert-Butyl 2-(4-(1-(4-fluorophenyl)-1H-pyrazol-4-yl)phenyl)morpholine-4-carboxylate (45 mg, 0.106 mmol) was dissolved in dioxane (0.2 ml) and a solution of HCl in dioxane (4M, 0.4 ml, 1.59 mmol) was added. The reaction mixture was stirred at 60° C. overnight. After cooling ether (2 ml) was added and the solid was filtered off. It was washed with ether and dried in vacuo to afford (S)-2-(4-(1-(4-fluorophenyl)-1H-pyrazol-4-yl)phenyl)morpholine hydrochloride (38 mg, 99%) as a white solid. MS (ISP): 324.2 ([M+H]$^+$).

Example 20

(S)-2-(4-(5-(4-Fluorophenyl)-1H-1,2,4-triazol-3-yl)phenyl)morpholine hydrochloride

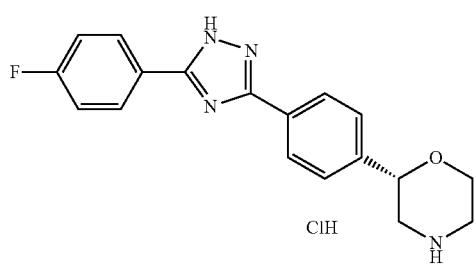 [SMILES: Fc1ccc(-c2nc(-c3ccc([C@H]4CNCCO4)cc3)n[nH]2)cc1 ; Cl]

a) (S)-tert-Butyl 2-(4-cyanophenyl)morpholine-4-carboxylate

A mixture of (S)-tert-butyl 2-(4-bromophenyl)morpholine-4-carboxylate (400 mg, 1.17 mmol), tetrakis(triphenylphosphine)palladium(0) (405 mg, 0.35 mmol) and zinc cyanide (206 mg, 1.75 mmol) in dimethylformamide (6 ml) was degassed with argon and heated in a closed tube at 85° C. on a Büchi shaker overnight. After cooling water (30 ml) was added, and the reaction mixture was extracted with ethyl acetate (50 ml). The aqueous phase was re-extracted with ethyl acetate (50 ml). The combined organic layers were re-extracted with conc. Sodium chloride solution, dried (MgSO4) and evaporated. The residue was purified by flash chromatography (20 g silica gel, 10% ethyl acetate in heptane) to yield a white solid (233 mg, 69%). MS (ISP): 289.1 ([M+H]$^+$), 306.2 ([M+NH4]$^+$).

b) (S)-tert-Butyl 2-(4-(5-(4-fluorophenyl)-1H-1,2,4-triazol-3-yl)phenyl)morpholine-4-carboxylate 4-Fluorobenzhydrazide (50 mg, 0.324) an (S)-tert-butyl 2-(4-cyanophenyl)morpholine-4-carboxylate (112 mg, 0.389 mmol) and potassium carbonate (22.5 mg, 0.162 mmol) was dissolved in butan-1-ol (1 ml) and stirred in a closed vial for 3 h at 150° C. The vial was opened and heating was continued for another 15 min to evaporate most of the solvent.

The yellow residue was partitioned between water and ethyl acetate. The combined organic layers were dried (MgSO4) and evaporated. Flash chromatography (10 g silica gel, 10% to 30% ethyl acetate in heptane) yielded a white solid (30 mg, 22%). MS (ISP): 369.2 ([M-tBu+H]$^+$), 425.2 ([M+H]$^+$).

c) (S)-2-(4-(5-(4-Fluorophenyl)-1H-1,2,4-triazol-3-yl)phenyl)morpholine hydrochloride (S)-tert-Butyl 2-(4-(5-(4-fluorophenyl)-1H-1,2,4-triazol-3-yl)phenyl)morpholine-4-carboxylate (28 mg, 0.066 mmol) was dissolved in dioxane (0.5 ml) and a solution of HCl in dioxane (4M, 0.2 ml, 0.79 mmol) was added. The reaction mixture was stirred at 60° C. for 2 h. After cooling ether (2 ml) was added and the solid was filtered off. It was washed with ether and dried in vacuo to afford (S)-2-(4-(5-(4-fluorophenyl)-1H-1,2,4-triazol-3-yl)phenyl)morpholine hydrochloride (26 mg, 99%) as a white solid. MS (ISP): 325.2 ([M+H]$^+$).

Example 21

4-Fluoro-N-(6-(morpholin-2-yl)-1H-indazol-3-yl)benzamide hydrochloride

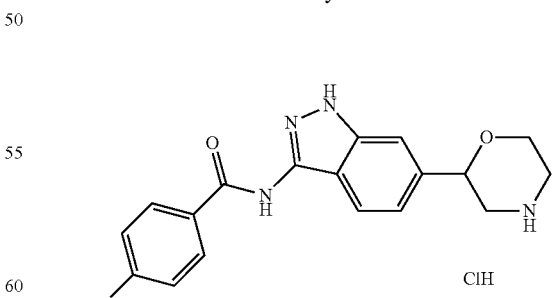

a) 2-(4-Bromo-3-fluoro-phenyl)-oxirane

2-Bromo-1-(4-bromo-3-fluorophenyl)-ethanone [CAS 1003879-02-4] (32.3 g, 109 mmol) was dissolved in ethanol (250 ml). The reaction mixture was cooled to 5° C. to give a yellow suspension. Sodiumborohydride (4.13 g, 109 mmol) was added over 5 min. The reaction mixture was stirred at room temperature for 1 hour. Sodium methoxide (2.95 g, 54.6 mmol) was added. The reaction mixture was stirred at 50° C. for 6 h. The reaction mixture was poured into tert.butyl methyl ether and extracted with brine. The organic layer was dried over $MgSO_4$ and concentrated in vacuo to yield a yellow oil (25.1 g, 94%). GC-EI-MS: 216 ([M.$^+$]).

b) 1-(4-Bromo-3-fluoro-phenyl)-2-(2-hydroxy-ethylamino)-ethanol 2-(4-Bromo-3-fluoro-phenyl)-oxirane (25.1 g, 109 mmol) was combined with tetrahydrofurane (70 ml) to give a yellow solution. Ethanolamine (66.4 g, 65.1 ml, 1.09 mol) was added. The resulting orange solution was stirred at room temperature overnight. The reaction mixture was poured into brine and extracted twice with ethyl acetate. The organic layers were dried over $MgSO_4$ and concentrated in vacuo to yield a yellow oil (27.9 g, 92%), MS (ISP): 277.9 ([{$^{79}$Br}M+H]$^+$), 279.9 ([{$^{81}$Br}M+H]$^+$).

c) [2-(4-Bromo-3-fluoro-phenyl)-2-hydroxy-ethyl]-carbamic acid tert-butyl ester 1-(4-Bromo-3-fluoro-phenyl)-2-(2-hydroxy-ethylamino)-ethanol (27.9 g, 100 mmol) was dissolved in tetrahydrofurane (200 ml) and coled to 0° C. Di-tert-butyl dicarbonate (24.1 g, 110 mmol) was added and the ice bath was removed. The reaction mixture was stirred at room temperature for 20 h. The reaction mixture was poured into water and extracted with dichloromethane. The reaction mixture was poured into EtOAc and extracted with diluted NaOH and brine. The organic layer was dried over $MgSO_4$ and concentrated in vacuo. The crude material was purified by flash chromatography (silica gel, 0% to 10% methanol in dichloromethane) to yield 25.3 g (66.5%) [2-(4-bromo-3-fluoro-phenyl)-2-hydroxy-ethyl]-(2-hydroxy-ethyl)-carbamic acid tert-butyl ester as a yellow oil, MS (ISP): 322.0 ([{$^{79}$Br}M-tBu+H]$^+$), 324.3 ([{$^{81}$Br}M-tBu+H]$^+$), 378.1 ([{$^{79}$Br}M+H]$^+$), 380.1 ([{$^{81}$Br}M+H]$^+$).

d) 2-(4-Bromo-3-fluoro-phenyl)-morpholine-4-carboxylic acid tert-butyl ester

[2-(4-Bromo-3-fluoro-phenyl)-2-hydroxy-ethyl]-(2-hydroxy-ethyl)-carbamic acid tert-butyl ester (25.3 g, 66.9 mmol) and triuethylamine (10.2 g, 14.0 ml, 100 mmol) were combined with tetrahydrofurane (270 ml) to give a light yellow solution. The reaction mixture was cooled to 0-5° C. and methanesulfonyl chloride (8.43 g, 5.73 ml, 73.6 mmol) was added dropwise. The reaction mixture was stirred at room temperature for 1 h to give a white suspension. The reaction mixture was filtered and washed with tetrahydrofurane (20 ml). Potassium 2-methyl-2-butoxide (1.7 M in toluene, 59 ml, 100 mmol) was added dropwise to the filtrate at 0-5° C. The reaction mixture was stirred at room temperature for 30 min. The reaction mixture was poured into ethyl acetate and extracted with dilute aqueous hydrochloric acid (pH 5), water and brine. The organic layer was dried over $MgSO_4$ and concentrated in vacuo to give a yellow oil which was further purified by flash chromatography (silica gel, heptane/ethyl acetate 4:1): yellow solid (19.5 g, 81%), MS (ISP): 259.9 ([{$^{79}$Br}M-BOC+H]$^+$), 261.9 ([{$^{81}$Br}M-BOC+H]$^+$).

e) tert-Butyl 2-(4-cyano-3-fluorophenyl)morpholine-4-carboxylat

To a 20 mL microwave vial were added 2-(4-bromo-3-fluoro-phenyl)-morpholine-4-carboxylic acid tert-butyl ester (1.5 g, 4.16 mmol) N-methyl-pyrrolidone (10 ml) and copper (I)-cyanide (559 mg, 6.25 mmol). The vial was capped and heated in a microwave synthesizer (Personal Chemistry Emrys Optimizer) at 180° C. for 30 min. The reaction mixture was poured into tert-butylmethylether (150 ml) and extracted with brine (3×50 mL). The organic layers were dried over MgSO4 and concentrated in vacuo. The crude material was purified by flash chromatography (silica gel, 50 g, 0% to 70% ethyl acetate in heptane) to yield a yellow solid (101 mg, 8%), MS (ISP): 307.2 ([M+H]$^+$).

f) tert-Butyl 2-(3-amino-1H-indazol-6-yl)morpholine-4-carboxylate

Hydrazine monohydrate (47.6 mg, 0.046 ml, 0.95 mmol) and tert-butyl 2-(4-cyano-3-fluorophenyl) morpholine-4-carboxylate (97 mg, 0.32 mmol) were dissolved in ethanol (1 ml) and the reaction mixture was refluxed overnight. After cooling, the solvent was evaporated and the product was extracted with water (3 ml) and ethyl acetate (5 ml). The organic layer was dried over $MgSO_4$ and concentrated in vacuo to give a yellow oil which was further purified by flash chromatography (silica gel, ethyl acetate). The product was isolated as a yellow oil (49 mg, 49%), MS (ISP): 219.2 (100%, [M-BOC+H]$^+$), 263.2 (80%, [M-tBu+H]$^+$), 319.2 (30%, [M+H]$^+$).

g) tert-Butyl 2-(3-(4-fluorobenzamido)-1H-indazol-6-yl)morpholine-4-carboxylate

Tert-butyl 2-(3-amino-1H-indazol-6-yl)morpholine-4-carboxylate (43 mg, 0.135 mmol) was dissolved in pyridine (0.2 ml) and the solution was cooled to −5° C. 4-fluorobenzoyl chloride (21.4 mg, 0.135 mmo) was slowly added. After 5 min, the cooling bath was removed and stirring was continuing overnight. The reaction mixture was diluted with ethylacetate (2 ml) and washed with 1M citric acid solution (2 ml). The organic layer was dried over MgSO4 and concentrated in vacuo to give a brown oil which was further purified by flash column chromatography (silica gel, 50% to 100% ethyl acetate in heptane). The product was isolated as a yellow solid (40 mg, 67%), MS (ISP): 441.3 (100%, ([M-tBu+H]$^+$), 385.2 (38%, [M+H]$^+$).

h) 4-Fluoro-N-(6-(morpholin-2-yl)-1H-indazol-3-yl) benzamide hydrochloride

Tert-butyl 2-(3-(4-fluorobenzamido)-1H-indazol-6-yl) morpholine-4-carboxylate (40 mg, 0.09 mmol) was dissolved in dioxane (0.2 ml) and a solution of HCl in dioxane (4M, 0.34 ml, 1.36 mmol) was added. The reaction mixture was stirred for 2 h at 60° C. After cooling ether (2 ml) was added, the mixture was stirred for 30 min and the solid was filtered off. It was washed with ether and dried in vacuo to afford 4-fluoro-N-(6-(morpholin-2-yl)-1H-indazol-3-yl)benzamide hydrochloride (22 mg, 66%) as an off-white solid. MS (ISP): 341.2 ([M+H]$^+$).

Example 22

(S)-2-{4-[(R)-4-(4-Fluoro-phenyl)-4,5-dihydro-oxazol-2-yl]-phenyl}-morpholine

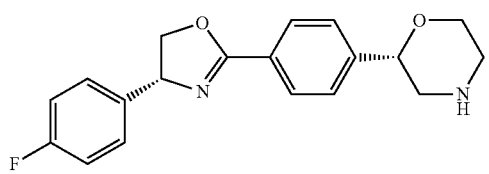 [SMILES: Fc1ccc([C@@H]2COC(c3ccc([C@H]4CNCCO4)cc3)=N2)cc1]

a) (S)-tert-butyl 2-(4-((R)-1-(4-fluorophenyl)-2-hydroxyethylcarbamoyl)phenyl)morpholine-4-carboxylate A mixture of (R)-2-amino-2-(4-fluorophenyl)ethanol (68.6 mg, 0.44 mmol), (S)-4-(4-(tert-butoxycarbonyl)morpholin-2-yl)benzoic acid [CAS 1131220-40-0], (136 mg, 0.44 mmol), 1-ethyl-3-(3-dimethylaminopropyl)carbodiimide (170 mg, 0.88 mmol), 4-dimethylaminopyridine (54.0 mg, 0.44 mmol) and triethylamine (179 mg, 0.25 ml, 1.77 mmol) in dichloromethane (9 ml) was stirred at room temperature overnight. The reaction was quenched by addition of 1M citric acid solution (5 ml). The organic layer was separated, washed with sodium bicarbonate saturated solution (5 ml), dried over MgSO4 and evaporated. The crude material was purified by flash chromatography (silica gel, gradient heptane/ethyl acetate), to give a white foam (100 mg, 51%), MS (ISP): 445.4 (100%, [M-tBu+H]$^+$), 389.3 (29%, [M+H]$^+$).

b) N—((R)-1-(4-Fluorophenyl)-2-hydroxyethyl)-4-((S)-morpholin-2-yl)benzamide (S)-tert-butyl 2-(4-((R)-1-(4-fluorophenyl)-2-hydroxyethylcarbamoyl)phenyl)morpholine-4-carboxylate (44 mg, 0.099 mmol) was dissolved in dichloromethane (0.3 ml) and trifluoracetic acid (447 mg, 0.3 ml, 3.92 mmol) was added. The reaction mixture was stirred at room temperature for 60 min. The solvent and excess of trifluoracetic acid were evaporated. The residue was dissolved in dichloromethane (3 ml) and extracted with odium bicarbonate saturated solution (2 ml). The organic layer was dried over MgSO4 and evaporated. The crude product was directly used for the next step. MS (ISP): 345.1 ([M+H]$^+$).

c) (S)-2-{4-[(R)-4-(4-Fluoro-phenyl)-4,5-dihydro-oxazol-2-yl]-phenyl}-morpholine N—((R)-1-(4-Fluorophenyl)-2-hydroxyethyl)-4-((S)-morpholin-2-yl)benzamide (14.4 mg, 0.042 mmol) was dissolved in dichloromethane (0.4 ml) and diethylaminosulfur trifluoride (DAST) (6.74 mg, 0.042 mmol) was added. The reaction mixture was allowed to stir at room temperature for 5 hours. The reaction mixture was poured over crushed ice mixed with 25% ammonium hydroxide solution (10 ml) and the solution was extracted twice with dichloromethane (2×10 ml). The combined organic layer was dried over MgSO4 and evaporated to give a sticky solid. Addition of heptane/ethylacetate 4:1 and some drops of dichloromethane gave a white solid which was isolated by filtration and dried in vacuo to afford the product as a white solid (5.1 mg, 37%): MS (ISP): 327.2 ([M+H]$^+$).

Example 23

(R)-2-(4-(5-(4-Fluorophenyl)-1H-1,2,4-triazol-3-yl)phenyl)morpholine hydrochloride

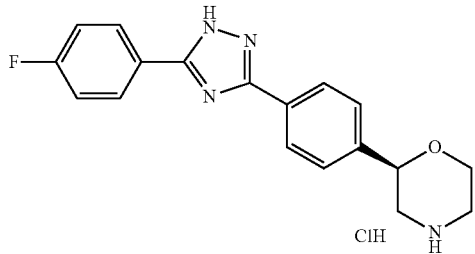 [SMILES: Fc1ccc(-c2nc(-c3ccc([C@@H]4CNCCO4)cc3)n[nH]2)cc1 ; Cl]

The title compound was obtained in analogy to example 20 using (R)-tert-butyl 2-(4-bromophenyl)morpholine-4-carboxylate instead of (S)-tert-butyl 2-(4-bromophenyl)morpholine-4-carboxylate in step a). White solid. MS (ISP): 325.2 ([M+H]$^+$).

Example 24

(S)-2-(4-(5-(Tetrahydro-2H-pyran-4-yl)-1H-pyrazol-3-yl)phenyl)morpholine hydrochloride

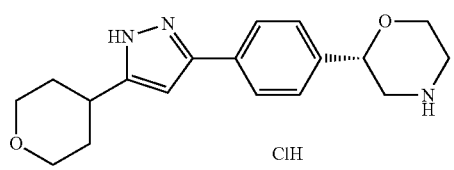 [SMILES: c1cc([C@H]2CNCCO2)ccc1-c1cc(C2CCOCC2)[nH]n1 ; Cl]

The title compound was obtained in analogy to example 3 using tetrahydro-2H-pyran-4-carbonyl chloride instead of 4-chlorobenzoyl chloride in step b). White solid. MS (ISP): 314.2 ([M+H]$^+$).

Example 25

(S)-2-(4-(3-(4-Fluorophenyl)-1H-1,2,4-triazol-1-yl)phenyl)morpholine hydrochloride

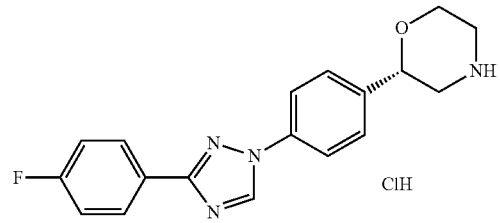 [SMILES: Fc1ccc(-c2ncn(-c3ccc([C@H]4CNCCO4)cc3)n2)cc1 ; Cl]

a) (S)-tert-butyl 2-(4-(3-(4-fluorophenyl)-1H-1,2,4-triazol-1-yl)phenyl)morpholine-4-carboxylate 3-(4-Fluorophenyl)-1H-1,2,4-triazole (CAS [95728-10-2], 200 mg, 0.9 mmol) was dissolved in a mixture of dimethylformamide and water (5.5 ml; v/v=10:1) and (S)-tert-butyl 2-(4-bromophenyl)morpholine-4-carboxylate (368 mg, 1.08 mmol), cesium carbonate (1.46 g, 4.48 mmol), copper(I)-iodide (5.1 mg, 0.027 mmol) and 8-hydroxyquinoline (4 mg, 0.027 mmol) were added successively. The glass was closed and the reaction mixture was allowed to stir at 150° C. for 48 h. According to TLC, the reaction was finished. After cooling, water and ethyl acetate were added. The organic layer was dried over MgSO4 and evaporated. The crude material was purified by flash chromatography (silica gel, gradient heptane/ethyl acetate), off-white solid (205 mg, 54%), MS (ISP): 425.2 ([M+H]$^+$).

b) (S)-2-(4-(3-(4-Fluorophenyl)-1H-1,2,4-triazol-1-yl)phenyl)morpholine hydrochloride (S)-tert-butyl 2-(4-(3-(4-fluorophenyl)-1H-1,2,4-triazol-1-yl)phenyl)morpholine-4-carboxylate (201 mg, 0.47 mmol) was dissolved in dioxane (0.5 ml) and a solution of HCl in dioxane (4M, 1.75 ml, 7.1 mmol) was added. The reaction mixture was stirred for 3 h at 60° C. After cooling ether (2 ml) was added and the solid was filtered off. It was washed with ether and dried in vacuo to afford (S)-2-(4-(3-(4-fluorophenyl)-1H-1,2,4-triazol-1-yl)phenyl)morpholine hydrochloride as a white solid (170 mg, 99%). MS (ISP): 325.2 ([M+H]⁺).

Example 26

(R)-2-(4-(1-(4-Fluorophenyl)-1H-pyrazol-4-yl)phenyl)morpholine hydrochloride

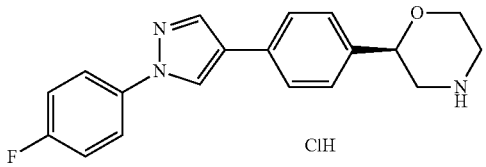 [SMILES: Fc1ccc(-n2cc(-c3ccc([C@@H]4CNCCO4)cc3)cn2)cc1 ; Cl]

The title compound was obtained in analogy to example 19 using (R)-tert-butyl 2-(4-bromophenyl)morpholine-4-carboxylate instead of (S)-tert-butyl 2-(4-bromophenyl)morpholine-4-carboxylate in step a). White solid. MS (ISP): 324.3 ([M+H]⁺).

Example 27

(S)-2-(4-(4-(4-Fluorophenyl)-1H-1,2,3-triazol-1-yl)phenyl)morpholine hydrochloride

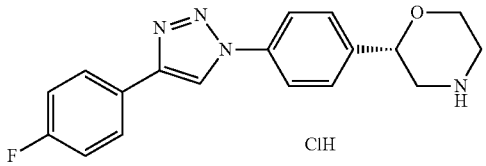 [SMILES: Fc1ccc(-c2cn(-c3ccc([C@H]4CNCCO4)cc3)nn2)cc1 ; Cl]

a) (S)-tert-Butyl 2-(4-(4-(4-fluorophenyl)-1H-1,2,3-triazol-1-yl)phenyl)morpholine-4-carboxylate (S)-tert-Butyl 2-(4-aminophenyl)morpholine-4-carboxylate (150 mg, 0.54 mol) was dissolved in 3 M acetic acid, then cooled to 0° C. Sodium nitrite (93 mg, 1.35 mmol) was added and the yellow solution was stirred at 0° C. for 5 min. Then sodium azide (70 mg, 1.08 mmol) was added to the mixture and stirring was continued for 15 min. Ethyl acetate was added to dissolve the precipitate and stirring was continued for 15 min. The organic layer was separated and the aqueous layer was re-extracted with ethyl acetate. The combined organic layers were extracted with 0.1M citric acid solution and with 1M sodium bicarbonate solution subsequently. After drying with MgSO4 the organic layer was evaporated to yield crude (S)-tert-butyl 2-(4-azidophenyl)morpholine-4-carboxylate as an yellow oil (161 mg) which was used for the following cycloaddition reaction.

(S)-tert-Butyl 2-(4-azidophenyl)morpholine-4-carboxylate (76 mg, 0.25 mol) was dissolved in diisopropylethylamine (800 mg, 6.24 mmol). 1-Ethynyl-4-fluorobenzene (30 mg, 0.25 mmol) was added, followed by copper(I)-iodide (48 mg, 0.25 mmol). The mixture was stirred for 2 h at room temperature. The green mixture was concentrated on the rotavap, silica gel (0.5 g) was added and after short grinding the mixture was put on a silica gel column for purification. Flash chromatography (5 g silica gel, 10 to 30% ethyl acetate in heptane) yielded a white solid (17 mg, 16%), MS (ISP): 425.2 ([M+H]⁺).

b) (S)-2-(4-(4-(4-Fluorophenyl)-1H-1,2,3-triazol-1-yl)phenyl)morpholine hydrochloride (S)-tert-Butyl 2-(4-(4-(4-fluorophenyl)-1H-1,2,3-triazol-1-yl)phenyl) morpholine-4-carboxylate (14 mg, 0.033 mmol) was dissolved in dioxane (0.5 ml) and a solution of HCl in dioxane (4M, 0.2 ml, 0.8 mmol) was added. The reaction mixture was stirred for 5 h at 60° C. After cooling ether (2 ml) was added and the solid was filtered off. It was washed with ether and dried in vacuo to afford (S)-2-(4-(4-(4-fluorophenyl)-1H-1,2,3-triazol-1-yl)phenyl)morpholine hydrochloride (10 mg, 84%) as a white solid. MS (ISP): 325.2 ([M+H]⁺).

Example 28

(S)-4-(3-(4-(Morpholin-2-yl)phenyl)-1H-pyrazol-5-yl)benzonitrile hydrochloride

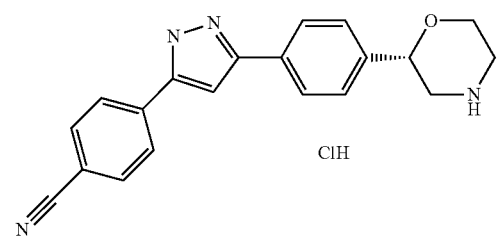 [SMILES: N#Cc1ccc(-c2cc(-c3ccc([C@H]4CNCCO4)cc3)n[nH]2)cc1 ; Cl]

The title compound was obtained in analogy to example 3 using (S)-tert-butyl 2-(4-bromophenyl)morpholine-4-carboxylate instead of tert-butyl 2-(4-bromophenyl)morpholine-4-carboxylate in step a) and 4-cyanobenzoyl chloride instead of 4-chlorobenzoyl chloride in step b). Off-white solid. MS (ISP): 331.2 ([M+H]⁺).

Example 29

(S)-2-(4-(5-(4-Fluorophenyl)-1H-pyrazol-3-yl)phenyl)morpholine hydrochloride

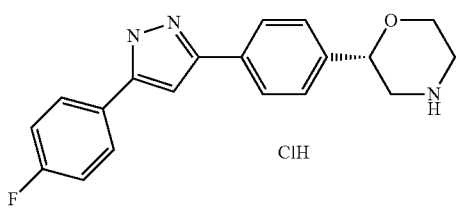 [SMILES: Fc1ccc(-c2cc(-c3ccc([C@H]4CNCCO4)cc3)n[nH]2)cc1 ; Cl]

The title compound was obtained in analogy to example 3 using (S)-tert-butyl 2-(4-bromophenyl)morpholine-4-carboxylate instead of tert-butyl 2-(4-bromophenyl)morpholine-4-carboxylate in step a) and 4-fluorobenzoyl chloride instead of 4-chlorobenzoyl chloride in step b). Off-white solid. MS (ISP): 324.3 ([M+H]⁺).

Example 30

(S)-4-Fluoro-N-(3-(4-(morpholin-2-yl)phenyl)-1H-pyrazol-5-yl)benzamide hydrochloride

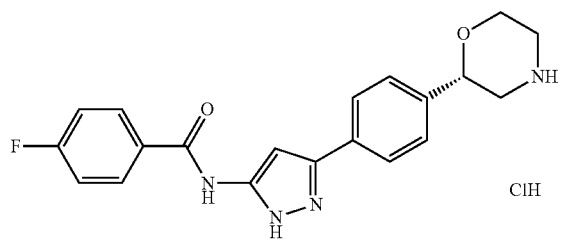 [SMILES: O=C(Nc1cc(-c2ccc([C@H]3CNCCO3)cc2)n[nH]1)c1ccc(F)cc1 ; Cl]

a) (S)-tert-Butyl 2-(4-(methoxycarbonyl)phenyl)morpholine-4-carboxylate (S)-4-(4-(tert-Butoxycarbonyl)morpholin-2-yl)benzoic acid [CAS 1131220-40-0], (500 mg, 1.63 mmol) was dissolved in dimethylformamide (8.6 ml). Potassium carbonate (675 mg, 4.88 mmol) and iodomethane (346 mg, 0.152 ml, 2.44 mmol) were added. The reaction mixture was shaken at room temperature overnight. The solution was diluted with water (25 ml) and extracted with ethyl acetate (2×40 ml). The combined organic layer was dried over MgSO4 and evaporated to give a light yellow oil. The crude material was purified by flash chromatography (silica gel, 25% ethyl acetate in heptane). Isolation of a white solid (427 mg, 82%), MS (ISP): 266.1 (100%, [M-tBu+H]$^+$), 222.1 (40%, [M-BOC+H]$^+$), 322.2 (7%[M+H]$^+$).

b) (S)-tert-Butyl 2-(4-(2-cyanoacetyl)phenyl)morpholine-4-carboxylate n-Butyllithium 1.6 M in hexane (1.63 ml, 2.61 mmol) was diluted with tetrahydrofuran (2 ml) and cooled to −78° C. Acetonitrile (107 mg, 0.137 ml, 2.61 mmol) was added dropwise and stirring was continuing for 1 hour. (S)-tert-butyl 2-(4-(methoxycarbonyl)phenyl)morpholine-4-carboxylate (420 mg, 1.31 mmol) dissolved in tetrahydrofuran was slowly added to the white slurry over a 10 min period. After 3 hours, the reaction was quenched by addition of saturated ammonium chloride solution (5 ml) and extracted with diethyl ether (10 ml). The organic layer was dried over MgSO4 and evaporated.

The crude material was purified by flash chromatography (silica gel, gradient heptane/ethylacetate) to obtained the product as a light yellow solid (360 mg, 83%), 1H NMR (300 MHz, CDCl3) δ ppm: 1.49 (s, 9H), 2-69-2.83 (m, 1H), 2.98-3.13 (m, 1H), 3.69 (td, J=9 Hz, J=0.5 Hz, 1H), 3.88-4.20 (m, 3H), 4.07 (s, 2H), 4.5 (dd, J=9 Hz, J=0.5 Hz), 7.54 (d, J=6.4 Hz), 7.92 (d, J=6.4 Hz).

c) (S)-tert-Butyl 2-(4-(5-amino-1H-pyrazol-3-yl)phenyl)morpholine-4-carboxylate S)-tert-Butyl 2-(4-(2-cyanoacetyl)phenyl)morpholine-4-carboxylate (340 mg, 1.03 mmol) was dissolved in ethanol (0.9 ml) and hydrazine monohydrate (124 mg, 0.120 ml, 2.47 mmol) was added. The reaction mixture was heated for 6 hours at 60° C. and was stirred at room temperature overnight. Evaporation of the solvent gave a foam which was crystallised by adding heptane/ethyl acetate: yellow solid, (320 mg, 90%)

MS (ISP): 289.1 (100%, [M-tBu+H]$^+$), 345.1 (26%[M+H]$^+$), 245.2 (9%, [M-BOC+H]$^+$).

d) (S)-tert-Butyl 2-(4-(5-(4-fluorobenzamido)-1H-pyrazol-3-yl)phenyl)morpholine-4-carboxylate (S)-tert-Butyl 2-(4-(5-amino-1H-pyrazol-3-yl)phenyl)morpholine-4-carboxylate (100 mg, 0.29 mmol) was dissolved in a mixture of tetrahydrofurane/dichloromethane 2:3 (1.5 ml) then pyridine (46 mg, 0.047 ml, 0.58 mmol) and 4-dimethylaminopyridine (1.7 mg, 0.014 mmol) were added at 0° C. After 5 min, 4-fluorobenzoyl chloride (55.2 mg, 0.348 mmol) was addded and the reaction mixture was stirred at 0° C. for 1 h. The cooling bath was removed and the reaction mixture was allowed to stir at room temperature overnight. The reaction was quenched by addition of 1M citric acid (3 ml) and was extracted with ethyl acetate (5 ml). The organic layer was dried over MgSO4 and evaporated. The crude material was purified by flash chromatography (silica gel, hepatne/ethyl acetate 1:1). Isolation of an off-white solid (100 mg, 74%), MS (ISP): 411.2 (100%, [M-tBu+H]$^+$), 467.2 (66%, [M+H]$^+$).

e) (S)-4-Fluoro-N-(3-(4-(morpholin-2-yl)phenyl)-1H-pyrazol-5-yl)benzamide hydrochloride (S)-tert-Butyl 2-(4-(5-amino-1H-pyrazol-3-yl)phenyl)morpholine-4-carboxylate (95 mg, 0.2 mmol) was dissolved in dioxane (0.8 ml) and a solution of HCl in dioxane (4M, 0.76 ml, 3.0 mmol) was added. The reaction mixture was stirred for 2 h at 60° C. After cooling ether (2 ml) was added, the mixture was stirred for 30 min and the solid was filtered off. It was washed with ether and dried in vacuo to afford (S)-4-fluoro-N-(3-(4-(morpholin-2-yl)phenyl)-1H-pyrazol-5-yl)benzamide hydrochloride (59 mg, 72%) as an off-white solid. MS (ISP): 367.2 ([M+H]$^+$).

Example 31

(R)-2-(4-(5-(4-Fluorophenyl)-1H-pyrazol-3-yl)phenyl)morpholine hydrochloride

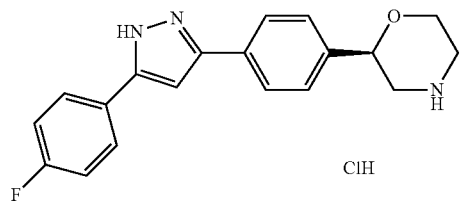 [SMILES: Fc1ccc(-c2cc(-c3ccc([C@@H]4CNCCO4)cc3)n[nH]2)cc1 ; Cl]

The title compound was obtained in analogy to example 3 using (R)-tert-butyl 2-(4-bromophenyl)morpholine-4-carboxylate instead of tert-butyl 2-(4-bromophenyl)morpholine- 4-carboxylate in step a) and 4-fluorobenzoyl chloride instead of 4-chlorobenzoyl chloride in step b). Off-white solid. MS (ISP): 324.2 ([M+H]⁺).

Example 32

(R)-4-(3-(4-(Morpholin-2-yl)phenyl)-1H-pyrazol-5-yl)benzonitrile hydrochloride

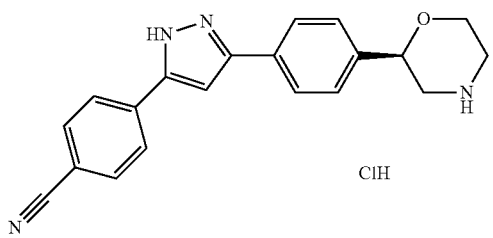 [SMILES: N#Cc1ccc(-c2cc(-c3ccc([C@@H]4CNCCO4)cc3)n[nH]2)cc1 ; Cl]

The title compound was obtained in analogy to example 3 using (R)-tert-butyl 2-(4-bromophenyl)morpholine-4-carboxylate instead of tert-butyl 2-(4-bromophenyl)morpholine-4-carboxylate in step a) and 4-cyanobenzoyl chloride instead of 4-chlorobenzoyl chloride in step b). Off-white solid. MS (ISP): 331.2 ([M+H]⁺).

Example 33

(S)-3-Fluoro-4-(3-(4-(morpholin-2-yl)phenyl)-1H-pyrazol-5-yl)benzonitrile hydrochloride

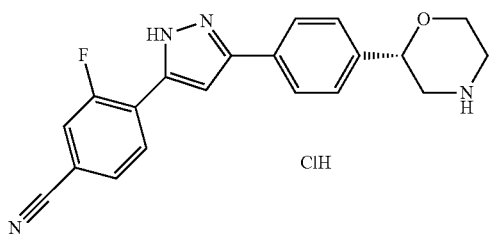 [SMILES: N#Cc1ccc(-c2cc(-c3ccc([C@H]4CNCCO4)cc3)n[nH]2)c(F)c1 ; Cl]

The title compound was obtained in analogy to example 3 using (S)-tert-butyl 2-(4-bromophenyl)morpholine-4-carboxylate instead of tert-butyl 2-(4-bromophenyl)morpholine-4-carboxylate in step a) and 4-cyano-2-fluorobenzoyl chloride instead of 4-chlorobenzoyl chloride in step b). Light-yellow solid. MS (ISP): 349.1 ([M+H]⁺).

Example 34

(R)-2-(4-(5-(4-Fluorophenyl)-1,3,4-oxadiazol-2-yl)phenyl)morpholine hydrochloride

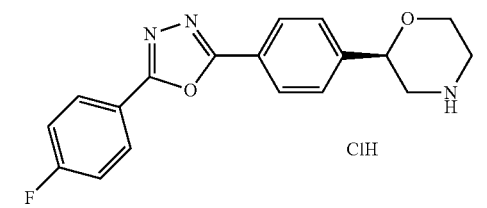 [SMILES: Fc1ccc(-c2nnc(-c3ccc([C@@H]4CNCCO4)cc3)o2)cc1 ; Cl]

The title compound was obtained in analogy to example 17 using (R)-tert-butyl 2-(4-formylphenyl)morpholine-4-carboxylate instead of (S)-tert-butyl 2-(4-formylphenyl)morpholine-4-carboxylate in step a). White solid. MS (ISP): 326.2 ([M+H]⁺).

Example 35

(R)-2-(4-(1-(4-Fluorophenyl)-1H-1,2,3-triazol-4-yl)phenyl)morpholine hydrochloride

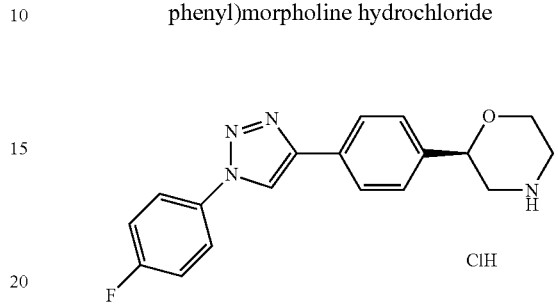

The title compound was obtained in analogy to example 18 using (R)-tert-butyl 2-(4-formylphenyl)morpholine-4-carboxylate instead of (S)-tert-butyl 2-(4-formylphenyl)morpholine-4-carboxylate in step a). Off-white solid. MS (ISP): 325.2 ([M+H]⁺).

Example 36

(R)-2-(4-(3-(4-Fluorophenyl)-1H-1,2,4-triazol-1-yl)phenyl)morpholine hydrochloride

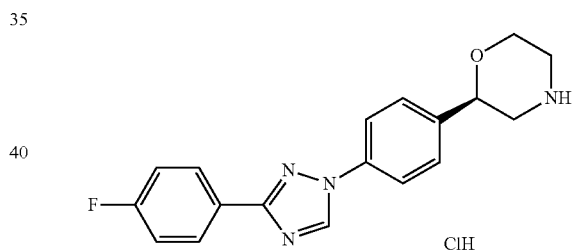

The title compound was obtained in analogy to example 25 using (R)-tert-butyl 2-(4-bromophenyl)morpholine-4-carboxylate instead of (S)-tert-butyl 2-(4-bromophenyl)morpholine-4-carboxylate in step a). White solid. MS (ISP): 325.2 ([M+H]⁺).

Example 37

(S)-2-{4-[5-(6-Chloro-pyridin-3-yl)-1H-pyrazol-3-yl]-phenyl}-morpholine hydrochloride

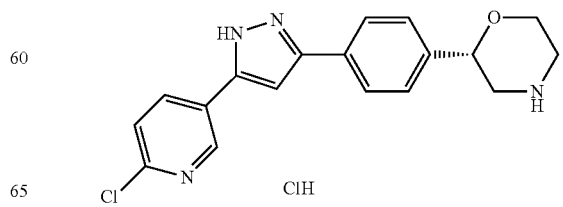

The title compound was obtained in analogy to example 3 using (S)-tert-butyl 2-(4-bromophenyl)morpholine-4-carboxylate instead of tert-butyl 2-(4-bromophenyl)morpholine-4-carboxylate in step a) and 6-chloronicotinoyl chloride instead of 4-chlorobenzoyl chloride in step b). Light yellow solid. 341.2 ([{$^{35}$Cl}M+H]$^+$), 343.3 ([{$^{37}$Cl}M+H]$^+$).

Example 38

(R)-2-{4-[5-(6-Chloro-pyridin-3-yl)-1H-pyrazol-3-yl]-phenyl}-morpholine hydrochloride

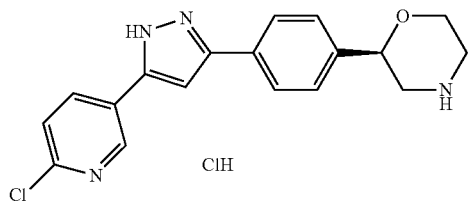 [SMILES: Clc1ccc(-c2cc(-c3ccc([C@@H]4CNCCO4)cc3)n[nH]2)cn1 ; Cl]

The title compound was obtained in analogy to example 3 using (R)-tert-butyl 2-(4-bromophenyl)morpholine-4-carboxylate instead of tert-butyl 2-(4-bromophenyl)morpholine-4-carboxylate in step a) and 6-chloronicotinoyl chloride instead of 4-chlorobenzoyl chloride in step b). Light yellow solid. 341.2 ([{$^{35}$Cl}M+H]$^+$), 343.2 ([{$^{37}$Cl}M+H]$^+$).

Example 39

(R)-2-(4-(4-(4-Fluorophenyl)-1H-1,2,3-triazol-1-yl)phenyl)morpholine hydrochloride

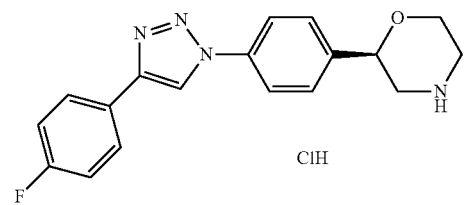 [SMILES: Fc1ccc(-c2cn(-c3ccc([C@@H]4CNCCO4)cc3)nn2)cc1 ; Cl]

The title compound was obtained in analogy to example 27 using (R)-tert-butyl 2-(4-aminophenyl)morpholine-4-carboxylate instead of (S)-tert-butyl 2-(4-aminophenyl)morpholine-4-carboxylate in step a). White solid. MS (ISP): 325.2 ([M+H]$^+$).

Example 40

(S)-2-(3-Fluoro-4-(5-(4-fluorophenyl)-1H-pyrazol-3-yl)phenyl)morpholine hydrochloride

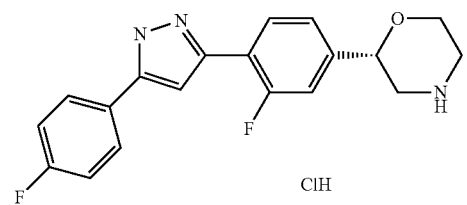 [SMILES: Fc1ccc(-c2cc(-c3ccc([C@H]4CNCCO4)cc3F)n[nH]2)cc1 ; Cl]

The title compound was obtained in analogy to example 3 using (S)-tert-butyl 2-(4-bromo-3-fluorophenyl)morpholine-4-carboxylate (racemate synthesis descibed in Example 21 followed by preparative chiral separation on Chiralpak AD using 4% isopropanol/heptane) instead of tert-butyl 2-(4-bromophenyl)morpholine-4-carboxylate in step a) and 4-fluorobenzoyl chloride instead of 4-chlorobenzoyl chloride in step b). Off-white solid. MS (ISP): 342.1 ([M+H]$^+$).

Example 41

(R)-2-(3-Fluoro-4-(5-(4-fluorophenyl)-1H-pyrazol-3-yl)phenyl)morpholine hydrochloride

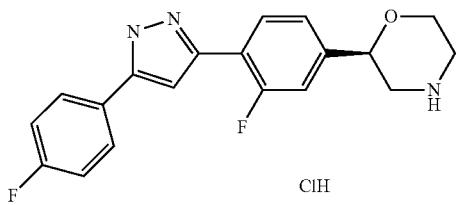 [SMILES: Fc1ccc(-c2cc(-c3ccc([C@@H]4CNCCO4)cc3F)n[nH]2)cc1 ; Cl]

The title compound was obtained in analogy to example 3 using (R)-tert-butyl 2-(4-bromo-3-fluorophenyl)morpholine-4-carboxylate (racemate synthesis descibed in Example 21 followed by preparative chiral separation on Chiralpak AD using 4% isopropanol/heptane) instead of tert-butyl 2-(4-bromophenyl)morpholine-4-carboxylate in step a) and 4-fluorobenzoyl chloride instead of 4-chlorobenzoyl chloride in step b). Off-white solid. MS (ISP): 342.1 ([M+H]$^+$).

Example 42

(S)-2-(4-(5-(2-Chloropyridin-4-yl)-1H-pyrazol-3-yl)phenyl)morpholine hydrochloride

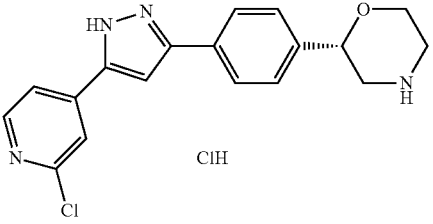 [SMILES: Clc1cc(-c2cc(-c3ccc([C@H]4CNCCO4)cc3)n[nH]2)ccn1 ; Cl]

The title compound was obtained in analogy to example 3 using (S)-tert-butyl 2-(4-bromophenyl)morpholine-4-carboxylate instead of tert-butyl 2-(4-bromophenyl)morpholine-4-carboxylate in step a) and 2-chloroisonicotinoyl chloride instead of 4-chlorobenzoyl chloride in step b). Light brown solid, MS (ISP): 341.2 ([{$^{35}$Cl}M+H]$^+$), 343.1 ([{$^{37}$Cl}M+H]$^+$).

Example 43

(S)-2-(2-(4-Fluorophenyl)-1H-benzo[d]imidazol-5-yl)morpholine hydrochloride

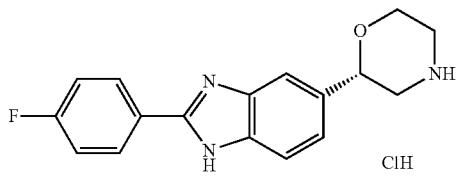 [SMILES: Fc1ccc(-c2nc3cc([C@H]4CNCCO4)ccc3[nH]2)cc1 ; Cl]

a) 4-Fluoro-N-(methylsulfonyloxy)benzimidoyl chloride

4-Fluorobenzaldehyde oxime (1.5 g, 10.8 mmol) was dissolved in a mixture of dimethylformamide (1 ml), tetrahydrofurane (10 ml) and chloroform (10 ml). N-chlorosuccinimide (1.51 g, 11.3 mmol) was added slowly keeping the temperature at 40° C. The mixture was stirred for 1 h, then quenched with water (10 ml). The aqueous layer was discarded and the organic layer was washed with water (10 ml). The organic layer was dried (MgSO4) and evaporated. The residue was dissolved in ethyl acetate (50 ml) and the solution was cooled to 0° C. Triethylamine (2.4 g, 23.7 mmol) was added and the mixture was stirred at 0° C. for 10 min to give a white slurry. Methanesulfonyl chloride (1.36 g, 11.9 mmol) was added slowly at 0° C., and the mixture was stirred at room temperature for 1 h. The crystals were filtered off, the filtrate was washed twice with water (10 ml), dried over MgSO4 and concentrated under reduced pressure.

Flash chromatography of the residue (50 g silica gel, 10 to 30% ethyl acetate in heptane) yielded a white solid (1.28 g, 47%); 1H NMR (300 MHz, CDCl3) δ ppm: 3.27 (s, 3H), 7.16 (t, J=9 Hz, 2H), 7.96 (dd, J=6 Hz, J=9 Hz, 2H).

b) (S)-tert-butyl 2-(2-(4-fluorophenyl)-1H-benzo[d]imidazol-5-yl)morpholine-4-carboxylate A solution of (S)-tert-butyl 2-(4-aminophenyl)morpholine-4-carboxylate (140 mg, 0.5 mol), 4-fluoro-N-(methylsulfonyloxy)benzimidoyl chloride (152 mg, 0.6 mmol) and N,N,N',N'-tetramethylethylenediamine (123 mg, 1.06 mmol) in tetrahydrofurane (0.8 ml) was shaken in a closed vial at 60° C. overnight. Water was added, and the mixture was extracted twice with ethyl acetate. The cobined organic layers were dried (MgSO4) and evaporated. Flash chromatography (10 g silica gel, 10 to 30% ethyl acetate in heptane) yielded a white solid (92 mg, 46%), MS (ISP): 398.2 ([M+H]+).

c) (S)-2-(2-(4-Fluorophenyl)-1H-benzo[d]imidazol-5-yl)morpholine hydrochloride (S)-tert-Butyl 2-(2-(4-fluorophenyl)-1H-benzo[d]imidazol-5-yl)morpholine-4-carboxylate (88 mg, 0.22 mmol) was dissolved in dioxane (1 ml) and a solution of HCl in dioxane (4M, 0.66 ml, 2.66 mmol) was added. The reaction mixture was stirred for 3 h at 60° C. After cooling ether (2 ml) was added and the solid was filtered off. It was washed with ether and dried in vacuo to afford (S)-2-(2-(4-fluorophenyl)-1H-benzo[d]imidazol-5-yl)morpholine hydrochloride (56 mg, 76%) as an off-white solid. MS (ISP): 298.2 ([M+H]+).

Example 44

(R)-2-(2-(4-Fluorophenyl)-1H-benzo[d]imidazol-5-yl)morpholine hydrochloride

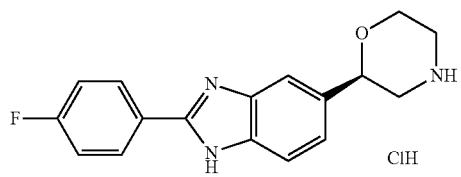 [SMILES: Fc1ccc(-c2nc3cc([C@@H]4CNCCO4)ccc3[nH]2)cc1 ; Cl]

The title compound was obtained in analogy to example 43 using (R)-tert-butyl 2-(4-aminophenyl)morpholine-4-carboxylate instead of (S)-tert-butyl 2-(4-aminophenyl)morpholine-4-carboxylate in step b). Off-white solid. MS (ISP): 298.2 ([M+H]+).

Example 45

(S)-2-(9H-Pyrido[2,3-b]indol-6-yl)morpholine hydrochloride

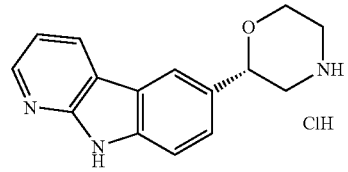 [SMILES: c1cnc2[nH]c3ccc([C@H]4CNCCO4)cc3c2c1 ; Cl]

a) (S)-tert-butyl 2-(4-(3-chloropyridin-2-ylamino)phenyl)morpholine-4-carboxylate (S)-tert-Butyl 2-(4-aminophenyl)morpholine-4-carboxylate (120 mg, 0.43 mol), 2,3-dichloropyridine (64 mg, 0.43 mmol) and cesium carbonate (211 mg, 0.647 mmol) were combined with dioxane (2 ml) to give a suspension. The mixture was degassed with argon for 5 min. Xanthphos (15 mg, 0.026 mmol) and tris(dibenzylideneacetone)dipalladium chloroform complex (13 mg, 0.013 mmol) were added. The reaction mixture was capped and stirred at 100° C. for 2 h. The crude reaction mixture was filtered through a syringe filter, concentrated in vacuo and purified by flash chromatography (20 g silica gel, 5 to 20% ethyl acetate in heptane) yielded a light yellow foam (88 mg, 53%); MS (ISP): 390.2 ([{35Cl}M+H]+), 392.2 ([{37Cl}M+H]+).

b) (S)-tert-butyl 2-(9H-pyrido[2,3-b]indol-6-yl)morpholine-4-carboxylate (S)-tert-Butyl 2-(4-(3-chloropyridin-2-ylamino)phenyl)morpholine-4-carboxylate (47 mg, 0.12 mmol), palladium (II)-acetate (2.7 mg, 0.012 mmol), tricyclohexylphosphine tetrafluoroborate (9 mg, 0.024 mmol) and DBU (37 mg, 0.24 mmol) were dissolved in a mixture of o-xylene (0.7 ml) and dimethylacetamide (0.7 ml). The mixture was degassed with argon for 5 min and heated at 155° C. for 16 h in a closed vial. After cooling, the reaction mixture was poured into water and extracted with ethyl acetate. The organic layer was dried over MgSO4 and evaporated. Flash chromatography (2 g silica gel, 10 to 30% ethyl acetate in heptane) yielded a white solid (22 mg, 52%), MS (ISP): 354.3 ([M+H]+).

c) (S)-2-(9H-Pyrido[2,3-b]indol-6-yl)morpholine hydrochloride (S)-tert-Butyl 2-(9H-pyrido[2,3-b]indol-6-yl)morpholine-4-carboxylate (22 mg, 0.062 mmol) was dissolved in dioxane (0.5 ml) and a solution of HCl in dioxane (4M, 0.19 ml, 0.75 mmol) was added. The reaction mixture was stirred for 2 h at 60° C. After cooling ether (2 ml) was added and the solid was filtered off. It was washed with ether and dried in vacuo to afford (S)-2-(9H-pyrido[2,3-b]indol-6-yl)morpholine hydrochloride (17 mg, 94%) as a light yellow solid. MS (ISP): 254.2 ([M+H]+).

Example 46

(S)-2-(3-(Trifluoromethyl)-9H-pyrido[2,3-b]indol-6-yl)morpholine hydrochloride

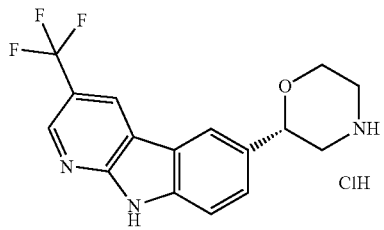 [SMILES: FC(F)(F)c1cnc2[nH]c3ccc([C@H]4CNCCO4)cc3c2c1 ; Cl]

The title compound was obtained in analogy to example 45 using 2,3-dichloro-5-(trifluoromethyl)pyridine instead of 2,3-dichloropyridine in step a). Off-white solid. MS (ISP): 322.2 ([M+H]+).

Example 47

(S)-2-(3-Chloro-9H-pyrido[2,3-b]indol-6-yl)morpholine hydrochloride

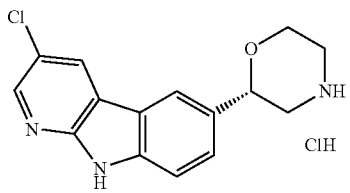 [SMILES: Clc1cnc2[nH]c3ccc([C@H]4CNCCO4)cc3c2c1 ; Cl]

The title compound was obtained in analogy to example 45 using 2,3,5-trichloro-pyridine instead of 2,3-dichloropyridine in step a). Light yellow solid. MS (ISP): 288.0 ([M+H]+).

Example 48

(R)-2-(3-(Trifluoromethyl)-9H-pyrido[2,3-b]indol-6-yl)morpholine hydrochloride

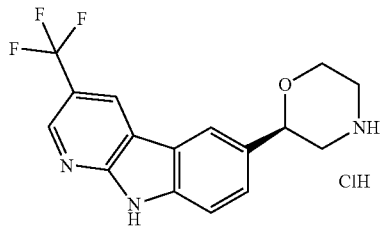 [SMILES: FC(F)(F)c1cnc2[nH]c3ccc([C@@H]4CNCCO4)cc3c2c1 ; Cl]

The title compound was obtained in analogy to example 45 using 2,3-dichloro-5-(trifluoromethyl)pyridine instead of 2,3-dichloropyridine and (R)-tert-butyl 2-(4-aminophenyl)morpholine-4-carboxylate instead of (S)-tert-butyl 2-(4-aminophenyl)morpholine-4-carboxylate in step a). Light yellow solid. MS (ISP): 322.2 ([M+H]+).

Example 49

(S)-2-(2-(Trifluoromethyl)-9H-pyrido[2,3-b]indol-6-yl)morpholine hydrochloride

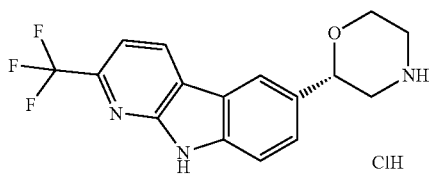 [SMILES: FC(F)(F)c1ccc2c(n1)[nH]c1ccc([C@H]3CNCCO3)cc12 ; Cl]

a) (S)-tert-Butyl 2-(4-amino-3-chlorophenyl)morpholine-4-carboxylate

In a 150 mL round-bottomed flask, (S)-tert-butyl 2-(4-aminophenyl)morpholine-4-carboxylate (5 g, 18 mmol) was dissolved in dimethylformamide (30 ml). N-Chlorosuccinimide (2.4 g, 18 mmol) was added and the mixture was stirred at 60° C. for 1 h. The reaction mixture was poured into ethyl acetate and extracted with saturated sodium chloride solution. The organic layers were dried over MgSO4 and concentrated in vacuo. The crude material was purified by flash chromatography (silica gel, 100 g, 30% ethyl acetate in heptane) to yield a light yellow solid (4.0 g, 71%) MS (ISP): 313.1 ([{35Cl}M+H]+), 315.1 ([{37Cl}M+H]+).

b) (S)-2-(2-(Trifluoromethyl)-9H-pyrido[2,3-b]indol-6-yl)morpholine hydrochloride The title compound was obtained in analogy to example 45 using 2-chloro-6-(trifluoromethyl)pyridine instead of 2,3-dichloropyridine and (S)-tert-butyl 2-(4-amino-3-chlorophenyl)morpholine-4-carboxylate instead of (S)-tert-butyl 2-(4-aminophenyl)morpholine-4-carboxylate in step a). Off-white solid. MS (ISP): 322.2 ([M+H]+).

Example 50

(R)-2-(3-(Trifluoromethyl)-9H-pyrido[2,3-b]indol-6-yl)morpholine hydrochloride

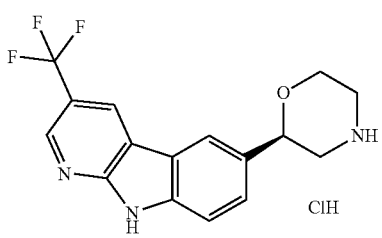 [SMILES: FC(F)(F)c1cnc2[nH]c3ccc([C@@H]4CNCCO4)cc3c2c1 ; Cl]

The title compound was obtained in analogy to example 49 using (R)-tert-butyl 2-(4-aminophenyl)morpholine-4-carboxylate instead of (S)-tert-butyl 2-(4-aminophenyl)morpholine-4-carboxylate in step a). Light yellow solid. MS (ISP): 322.2 ([M+H]+).

Example 51

(S)-2-(2-Isopropoxy-9H-pyrimido[4,5-b]indol-6-yl)morpholine hydrochloride

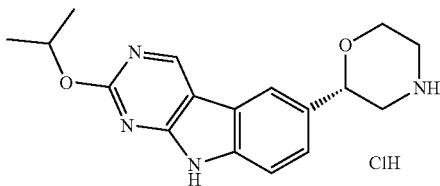 [SMILES: CC(C)Oc1ncc2c(n1)[nH]c1ccc([C@H]3CNCCO3)cc12 ; Cl]

a) (S)-tert-butyl 2-(4-(2,5-dichloropyrimidin-4-ylamino)phenyl)morpholine-4-carboxylate A mixture of (S)-tert-butyl 2-(4-aminophenyl)morpholine-4-carboxylate (100 mg, 0.36 mmol), 2,4,5-trichloropyrimidine (66 mg, 0.36 mmol) and diisopropylethylamine (70 mg, 0.54 mmol) was dissolved in 2-propanol (1.5 ml) and shaken at 80° C. overnight. Most of the solvent was evaporated. Ammonium chloride solution was added and the mixture was extracted with ethyl acetate twice. The combined organic layers are dried (MgSO4) and evaporated.

The residue was purified by column chromatography (silica gel, 10 to 30% ethyl acetate in heptane, 20 g ISCO column) to yield a white solid (342 mg, 75%) MS (ISP): 425.1 ([{35Cl}M+H]+), 427.2 ([{37Cl}M+H]+).

b) (S)-tert-butyl 2-(4-(5-chloro-2-isopropoxypyrimidin-4-ylamino)phenyl)morpholine-4-carboxylate To a stirred solution of potassium tert.-butoxide (116 mg, 1.03 mmol) in propan-2-ol (2 mL) was added (S)-tert-butyl 2-(4-(2,5-dichloropyrimidin-4-ylamino)phenyl)morpholine-4-carboxylate (110 mg, 0.26 mmol) and the mixture was shaken at 90° C. overnight. After cooling, the reaction mixture was poured into water and extracted with ethyl acetate. The organic layer was dried over MgSO4 and evaporated. The residue was purified by column chromatography (silica gel, 5 to 15% ethyl acetate in heptan, 10 g ISCO column). White foam (58 mg, 50%). MS (ISP): 449.3 ([{35Cl}M+H]+), 451.1 ([{37Cl}M+H]+).

c) (S)-tert-butyl 2-(2-isopropoxy-9H-pyrimido[4,5-b]indol-6-yl)morpholine-4-carboxylate (S)-tert-Butyl 2-(4-(5-chloro-2-isopropoxypyrimidin-4-ylamino)phenyl)morpholine-4-carboxylate (55 mg, 0.12 mmol), palladium-(II) acetate (2.8 mg, 0.012 mmol), tricyclohexylphopsphine tetrafluoroborate (9 mg, 0.024 mmol) and DBU (1,8-diazabicyclo[5.4.0]undec-7-ene; 37 mg, 0.245 mmol) were dissolved in a mixture of o-xylene (0.5 ml) and N,N-dimethylacetamide (0.5 ml). The mixture was degassed with Ar for 5 min, the vessel closed and heated at 155° C. for 16 h. The reaction mixture was poured into water and extracted with ethyl acetate. The organic layer was dried over MgSO4 and evaporated. The residue was purified by column chromatography (SiO2, 5 to 20% EtOAc in heptane, 2 g ISCO column). White solid (11 mg, 22%). MS (ISP): 413.3 ([M+H]+).

d) (S)-2-(2-Isopropoxy-9H-pyrimido[4,5-b]indol-6-yl)morpholine hydrochloride (S)-tert-Butyl 2-(2-isopropoxy-9H-pyrimido[4,5-b]indol-6-yl)morpholine-4-carboxylate (11 mg, 0.027 mmol) was dissolved in dioxane (0.5 ml) and a solution of HCl in dioxane (4M, 0.08 ml, 0.32 mmol) was added. The reaction mixture was stirred for 1 h at 60° C. After cooling ether (1 ml) was added and the solid was filtered off. It was washed with ether and dried in vacuo to afford (S)-2-(2-isopropoxy-9H-pyrimido[4,5-b]indol-6-yl)morpholine hydrochloride (6 mg, 64%) as an off-white solid. MS (ISP): 313.3 ([M+H]+).

Example 52

(R)-2-(6-Ethoxypyridin-3-yl)-6-(morpholin-2-yl)benzo[d]oxazole hydrochloride

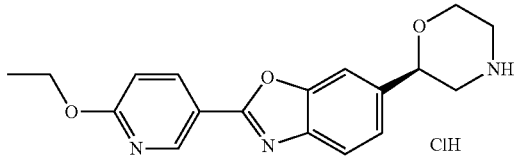 [SMILES: CCOc1ccc(-c2nc3ccc([C@@H]4CNCCO4)cc3o2)cn1 ; Cl]

a) (R)-tert-Butyl 2-(4-amino-3-bromophenyl)morpholine-4-carboxylate

In a 100 mL round-bottomed flask, (R)-tert-butyl 2-(4-aminophenyl)morpholine-4-carboxylate (4.3 g, 15.4 mmol) was dissolved in dimethylformamide (30 ml). N-Bromosuccinimide (2.75 g, 15.4 mmol) was added and the mixture was stirred at room temperature for 1 h. The reaction mixture was poured into ethyl acetate and extracted with saturated sodium chloride solution. The organic layers were dried over MgSO4 and concentrated in vacuo. The crude material was purified by flash chromatography (silica gel, 100 g, gradient 0-50% ethyl acetate in heptane) to yield a white solid (5.2 g, 94%), MS (ISP): 301.3 ([{79Br}M-tBu+H]+), 303.4 ([{81Br}M-tBu+H]+).

b) (R)-tert-Butyl 2-(3-bromo-4-(6-ethoxynicotinamido)phenyl)morpholine-4-carboxylate Under argon, 6-ethoxynicotinic acid (94 mg, 0.56 mmol) was suspended in dichloromethane (6.5 ml) and 1-chloro-N,N2-trimethylpropenylamine (93.5 mg, 0.7 mmol) was added dropwise and the mixture was stirred for 30 minutes at room temperature. In a second flask, (R)-tert-butyl 2-(4-amino-3-bromophenyl)morpholine-4-carboxylate (200 mg, 0.56 mmol) was dissolved in dichloromethane (5 ml) and ethyldiisopropylamine (181 mg, 1.4 mmol) was added. To this solution, the acid chloride solution formed in the first flask was added dropwise and the mixture was stirred at room temperature over 30 minutes. Water was added and the mixture was extracted with dichloromethane. The organic phase was dried over magnesium sulphate, filtered and concentrated in vacuo. The crude material was purified by flash chromatography (silica gel, 10 g, 10% to 50% EtOAc in heptane) to yield an off-white solid (260 mg, 92%), MS (ISP): 506.5 ([{79Br}M+H]+), 508.5 ([{81Br}M+H]+).

c) (R)-tert-Butyl 2-(2-(6-ethoxypyridin-3-yl)benzo[d]oxazol-6-yl)morpholine-4-carboxylate (R)-tert-Butyl 2-(3-bromo-4-(6-ethoxynicotinamido)phenyl)morpholine-4-carboxylate (100 mg, 0.2 mmol), cesium carbonate (130 mg, 0.4 mmol), 1,10-phenanthroline (3.6 mg, 0.02 mmol), copper(I) iodide (1.9 mg, 0.01 mmol) were mixed together in 1,2-dimethoxyethane (2 ml). The suspension was degassed with Argon and was heated overnight under Argon at 125° C. The mixture was cooled and poured into ethylacetate and filtered. The filtrate was absorbed on silica gel and separated by chromatography (gradient 10% to 50% EtOAc in heptane) to afford an off-white solid (34 mg, 40%). MS (ISP): 426.6 ([M+H]$^+$).

d) (R)-2-(6-Ethoxypyridin-3-yl)-6-(morpholin-2-yl)benzo[d]oxazole hydrochloride (R)-tert-Butyl 2-(2-(6-ethoxypyridin-3-yl)benzo[d]oxazol-6-yl)morpholine-4-carboxylate (31 mg, 0.073 mmol) was dissolved in dioxane (0.3 ml). Then a solution of HCl in dioxane (4M, 0.27 ml, 1.09 mmol) was added and the reaction mixture was stirred at 60° C. for 2 hours. After cooling, the solid was filtered off and washed with diethylether and dried in vacuo to afford (R)-2-(6-ethoxypyridin-3-yl)-6-(morpholin-2-yl)benzo[d]oxazole hydrochloride (15 mg, 58%) as a light yellow solid. MS (ISP): 326.6 ([M+H]$^+$).

Example 53

(R)-6-(Morpholin-2-yl)-2-(6-(trifluoromethyl)pyridin-3-yl)benzo[d]oxazole hydrochloride

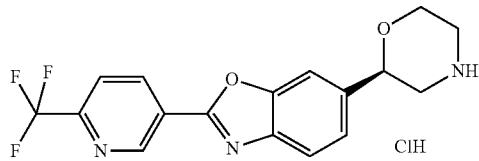 [SMILES: FC(F)(F)c1ccc(-c2nc3ccc([C@@H]4CNCCO4)cc3o2)cn1 ; Cl]

The title compound was obtained in analogy to example 52 using 6-(trifluoromethyl)nicotinic acid instead of 6-ethoxynicotinic acid in step b). White solid. MS (ISP): 350.6 ([M+H]$^+$).

Example 54

(R)-6-(Morpholin-2-yl)-2-(2-(trifluoromethyl)pyridin-4-yl)benzo[d]oxazole hydrochloride

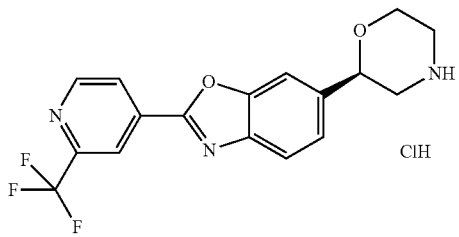 [SMILES: FC(F)(F)c1cc(-c2nc3ccc([C@@H]4CNCCO4)cc3o2)ccn1 ; Cl]

The title compound was obtained in analogy to example 52 using 2-(trifluoromethyl)-isonicotinic acid instead of 6-ethoxynicotinic acid in step b). Light brown foam. MS (ISP): 350.6 ([M+H]$^+$).

Example 55

(S)-6-(Morpholin-2-yl)-2-(2-(trifluoromethyl)pyridin-4-yl)benzo[d]oxazole hydrochloride

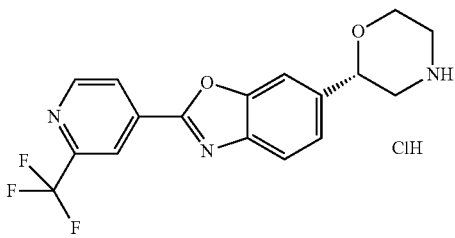 [SMILES: FC(F)(F)c1cc(-c2nc3ccc([C@H]4CNCCO4)cc3o2)ccn1 ; Cl]

The title compound was obtained in analogy to example 52 using (S)-tert-butyl 2-(4-aminophenyl)morpholine-4-carboxylate instead of (R)-tert-butyl 2-(4-aminophenyl)morpholine-4-carboxylate in step a) and 2-(trifluoromethyl)-isonicotinic acid instead of 6-ethoxynicotinic acid in step b). Light brown foam. MS (ISP): 350.6 ([M+H]$^+$).

The compounds of formula I and their pharmaceutically usable addition salts possess valuable pharmacological properties. Specifically, it has been found that the compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

(B) Radioligand Binding Assay on Rat TAAR1

Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated $K_d$ value, that was usually around 2.3 nM, resulting in the binding of approximately 0.2% of the radioligand and a specific binding representing approximately 85% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×$K_d$ in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

Example 56

(A) Radioligand Binding Assay on Mouse TAAR1

Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1,000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14,000 rpm for 20 s. The homogenate was centrifuged at 48,000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14,000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated $K_d$ value, that was usually around 0.7 nM, resulting in the binding of approximately 0.5% of the radioligand and a specific binding representing approximately 70% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×$K_d$ in nM and 500 µl of the membranes (resuspended at 60 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

The compounds show a $K_i$ value (µM) in mouse or rat on TAAR1 (in µM) as shown in the table below.

| Example | Ki (µM) mouse/rat |
| --- | --- |
| 1 | 0.038/0.76 |
| 2 | 0.0032/0.0711 |
| 3 | 0.001/0.0034 |
| 4 | 0.0012/0.0059 |
| 5 | 0.0044/0.0631 |
| 6 | 0.0019/0.0335 |
| 7 | 0.0089/0.0128 |
| 8 | 0.0004/0.002 |
| 9 | 0.0004/0.0021 |
| 10 | 0.0137/1.6626 |
| 11 | 0.009/0.0597 |
| 12 | 0.0005/0.0615 |
| 13 | 0.0003/0.0305 |
| 14 | 0.0008/0.183 |
| 15 | 0.0292/0.2846 |
| 16 | 0.0101/1.1445 |
| 17 | 0.0032/0.2285 |
| 18 | 0.002/0.2543 |
| 19 | 0.0015/0.0669 |
| 20 | 0.0012/0.0779 |
| 21 | 0.0617/0.895 |

-continued

| Example | Ki (μM) mouse/rat |
|---|---|
| 22 | 0.0318/1.5098 |
| 23 | 0.0015/0.0196 |
| 24 | >20/0.0722 |
| 25 | 0.0034/0.1402 |
| 26 | 0.0006/0.0122 |
| 27 | 0.0004/0.0565 |
| 28 | 0.001/0.0168 |
| 29 | 0.0007/0.0044 |
| 30 | 0.0022/0.3736 |
| 31 | 0.001/0.0036 |
| 32 | 0.0019/0.0154 |
| 33 | 0.0016/0.0201 |
| 34 | 0.004/0.156 |
| 35 | 0.0017/0.0252 |
| 36 | 0.0097/0.0857 |
| 37 | 0.004/0.3036 |
| 38 | 0.0027/0.0257 |
| 39 | 0.001/0.0322 |
| 40 | 0.0012/0.0155 |
| 41 | 0.0011/0.0043 |
| 42 | 0.0016/0.0171 |
| 43 | 0.0014/0.0291 |
| 44 | 0.004/0.0571 |
| 45 | 0.0277/1.0021 |
| 46 | 0.0023/0.0698 |
| 47 | 0.0032/0.075 |
| 48 | 0.0081/0.0639 |
| 49 | 0.0032/0.0182 |
| 50 | 0.0082/0.0303 |
| 51 | 0.0125/0.0904 |
| 52 | 0.0121/0.0873 |
| 53 | 0.0463/0.2261 |
| 54 | 0.2032/0.4479 |
| 55 | 0.0644/0.3036 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | | mg/tablet | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

Capsule Formulation

| Item | Ingredients | 5 mg | 25 mg | 100 mg | 500 mg |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

We claim:

1. A compound of formula

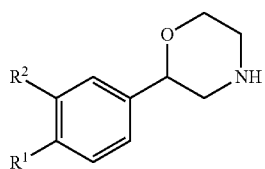

I wherein $R^1$ is a one or two membered heteroaryl group, selected from the group consisting of a)
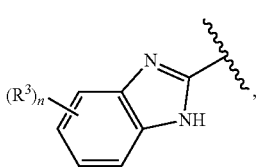

b)
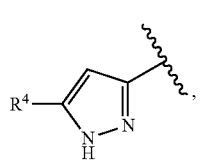

c)
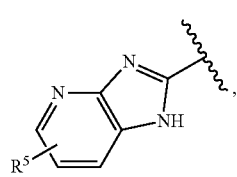

d)
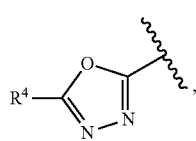

e)
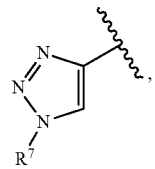

f)
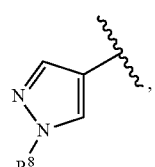

g)
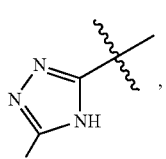

h)
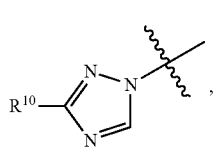

i)
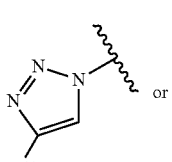 or j)
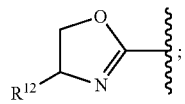;

$R^2$ is hydrogen or halogen; or $R^1$ and $R^2$ may form together with the carbon atoms to with they are attached the following rings k)
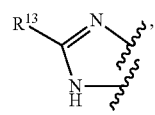

l)
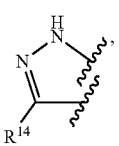

m)

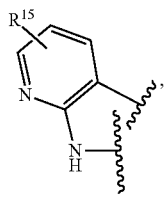

n)

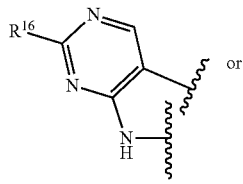 or o)

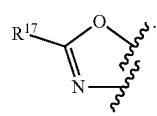

R³ is hydrogen, halogen or lower alkyl;
n is 1 or 2;
R⁴ is phenyl, optionally substituted by one or two substituents, selected from halogen or cyano, or is
pyridinyl, optionally substituted by halogen, or is
tetrahydropyran, or is
—NH—C(O)-phenyl, optionally substituted by halogen;
R⁵ is hydrogen or halogen;
R⁶-R¹³ are phenyl, optionally substituted by halogen:
R¹⁴ is —NH—C(O)-phenyl, substituted by halogen;
R¹⁵ is hydrogen, lower alkyl substituted by halogen or is halogen;
R¹⁶ is hydrogen or lower alkoxy;
R¹⁷ is pyridinyl, optionally substituted by lower alkoxy or lower alkyl substituted by halogen;
or a pharmaceutically suitable acid addition salt thereof, all racemic mixtures, all their corresponding enantiomers and/or optical isomers and all tautomeric forms of compounds of formula I.

2. A compound of formula Ia encompassed by formula I according to claim 1,

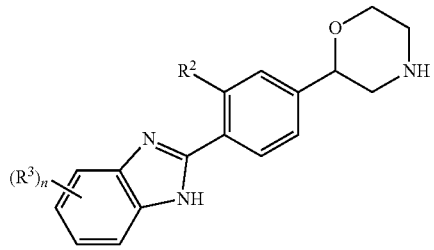

wherein
R² is hydrogen or halogen; and
R³ is hydrogen, halogen or lower alkyl;
n is 1 or 2;
or a pharmaceutically suitable acid addition salt thereof, all racemic mixtures, all their corresponding enantiomers and/or optical isomers and all tautomeric forms of compounds of formula I.

3. A compound of formula Ib encompassed by formula I according to claim 1

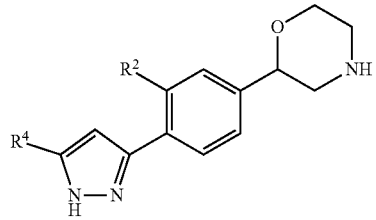

wherein
R² is hydrogen or halogen; and
R⁴ is phenyl, optionally substituted by one or two substituents, selected from halogen or cyano, or is
pyridinyl, optionally substituted by halogen, or is
tetrahydropyran, or is
—NH—C(O)-phenyl, optionally substituted by halogen;
or a pharmaceutically suitable acid addition salt thereof, all racemic mixtures, all their corresponding enantiomers and/or optical isomers and all tautomeric forms of compounds of formula I.

4. A compound of formula Ic encompassed by formula I according to claim 1,

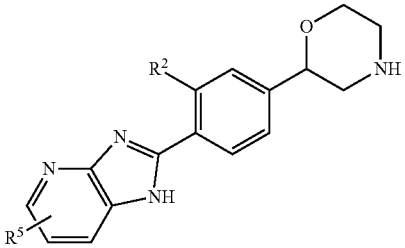

wherein
R² is hydrogen or halogen; and
R⁵ is hydrogen or halogen;
or a pharmaceutically suitable acid addition salt thereof, all racemic mixtures, all their corresponding enantiomers and/or optical isomers and all tautomeric forms of compounds of formula I.

5. A compound of formula Id encompassed by formula I according to claim 1,

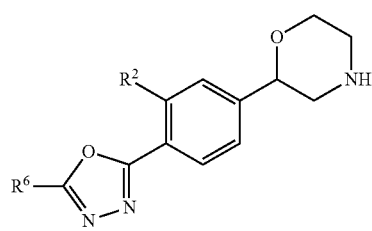

wherein
R² is hydrogen or halogen; and
R⁶ is phenyl, optionally substituted by halogen:
or a pharmaceutically suitable acid addition salt thereof, all racemic mixtures, all their corresponding enantiomers and/or optical isomers and all tautomeric forms of compounds of formula I.

6. A compound of formula Ie encompassed by formula I according to claim 1

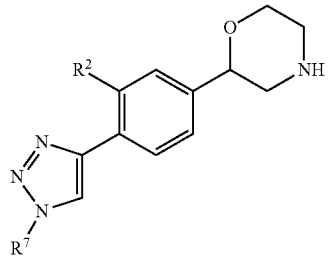

wherein
$R^2$ is hydrogen or halogen; or
$R^7$ is phenyl, optionally substituted by halogen:
or a pharmaceutically suitable acid addition salt thereof, all racemic mixtures, all their corresponding enantiomers and/or optical isomers and all tautomeric forms of compounds of formula I.

7. A compound of formula If encompassed by formula I according to claim 1,

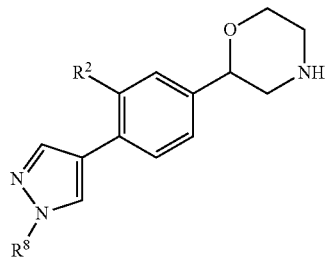

$R^2$ is hydrogen or halogen; and
$R^8$ is phenyl, optionally substituted by halogen:
or a pharmaceutically suitable acid addition salt thereof, all racemic mixtures, all their corresponding enantiomers and/or optical isomers and all tautomeric forms of compounds of formula I.

8. A compound of formula Ig encompassed by formula I according to claim 1

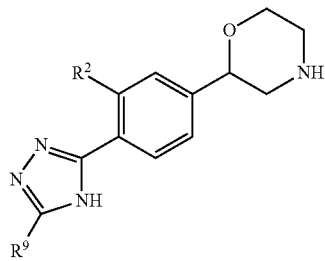

wherein
$R^2$ is hydrogen or halogen; and
$R^9$ is phenyl, optionally substituted by halogen:
or a pharmaceutically suitable acid addition salt thereof, all racemic mixtures, all their corresponding enantiomers and/or optical isomers and all tautomeric forms of compounds of formula I.

9. A compound of formula Ih encompassed by formula I according to claim 1,

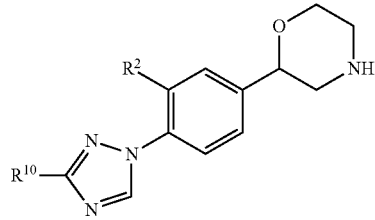

wherein
$R^2$ is hydrogen or halogen; or
$R^{10}$ is phenyl, optionally substituted by halogen:
or a pharmaceutically suitable acid addition salt thereof, all racemic mixtures, all their corresponding enantiomers and/or optical isomers and all tautomeric forms of compounds of formula I.

10. A compound of formula Ii encompassed by formula I according to claim 1,

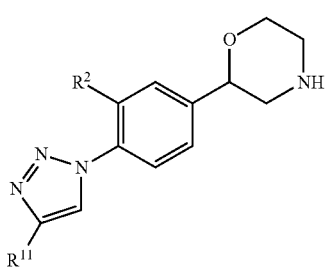

wherein
$R^2$ is hydrogen or halogen; and
$R^{11}$ is phenyl, optionally substituted by halogen:
or a pharmaceutically suitable acid addition salt thereof, all racemic mixtures, all their corresponding enantiomers and/or optical isomers and all tautomeric forms of compounds of formula I.

11. A compound of formula Ij encompassed by formula I according to claim 1,

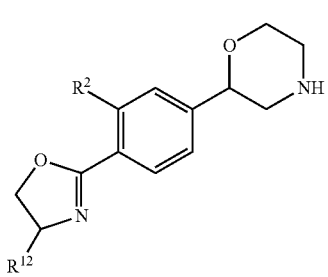

wherein
$R^2$ is hydrogen or halogen; and
$R^{12}$ is phenyl, optionally substituted by halogen:
or a pharmaceutically suitable acid addition salt thereof, all racemic mixtures, all their corresponding enantiomers and/or optical isomers and all tautomeric forms of compounds of formula I.

12. A compound of formula Ik encompassed by formula I according to claim 1,

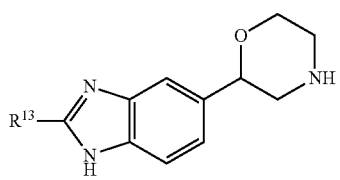

wherein

R$^{13}$ is phenyl, optionally substituted by halogen:

or a pharmaceutically suitable acid addition salt thereof, all racemic mixtures, all their corresponding enantiomers and/or optical isomers and all tautomeric forms of compounds of formula I.

13. A compound of formula Il encompassed by formula I according to claim 1, Ia Ib

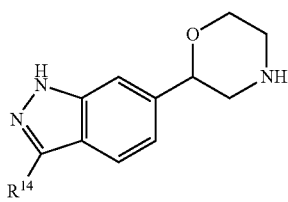

wherein

R$^{14}$ is —NH—C(O)-phenyl, substituted by halogen;

or a pharmaceutically suitable acid addition salt thereof, all racemic mixtures, all their corresponding enantiomers and/or optical isomers and all tautomeric forms of compounds of formula I.

14. A compound of formula Im encompassed by formula I according to claim 1,

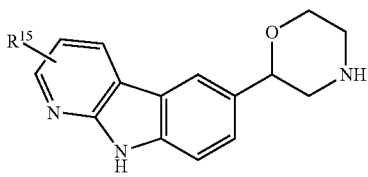

wherein

R$^{15}$ is hydrogen, lower alkyl substituted by halogen or halogen;

or a pharmaceutically suitable acid addition salt thereof, all racemic mixtures, all their corresponding enantiomers and/or optical isomers and all tautomeric forms of compounds of formula I.

15. A compound of formula In encompassed by formula I according to claim 1,

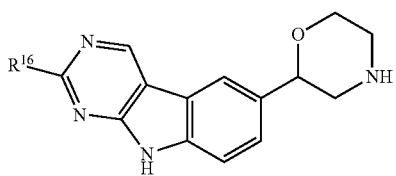

wherein

R$^{16}$ is hydrogen or lower alkoxy;

or a pharmaceutically suitable acid addition salt thereof, all racemic mixtures, all their corresponding enantiomers and/or optical isomers and all tautomeric forms of compounds of formula I.

16. A compound of formula Io encompassed by formula I according to claim 1,

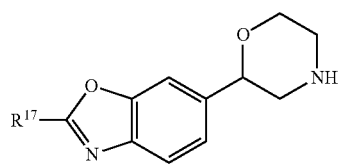

R$^{17}$ is pyridinyl, optionally substituted by lower alkoxy or lower alkyl substituted by halogen;

or a pharmaceutically suitable acid addition salt thereof, all racemic mixtures, all their corresponding enantiomers and/or optical isomers and all tautomeric forms of compounds of formula I.

17. A compound of formula I according to claim 1, which compounds are 2-(4-(1H-Benzo[d]imidazol-2-yl)phenyl)morpholine 2-(4-(6-Chloro-1H-benzo[d]imidazol-2-yl)phenyl)morpholine (S)-2-(4-(6-Fluoro-1H-benzo[d]imidazol-2-yl)phenyl) morpholine (S)-2-(4-(4,6-Difluoro-1H-benzo[d]imidazol-2-yl)phenyl)morpholine (R)-2-(4-(6-Fluoro-1H-benzo[d]imidazol-2-yl)phenyl) morpholine (S)-2-(4-(5,6-Dimethyl-1H-benzo[d]imidazol-2-yl)phenyl)morpholine 2-(4-(5-(4-Chlorophenyl)-1H-pyrazol-3-yl)phenyl)morpholine 2-(4-(5-(4-Fluorophenyl)-1H-pyrazol-3-yl)phenyl)morpholine 2-(4-(5-(6-Chloropyridin-3-yl)-1H-pyrazol-3-yl)phenyl) morpholine 4-(3-(4-(Morpholin-2-yl)phenyl)-1H-pyrazol-5-yl)benzonitrile (R)-2-(4-(5-(3-Chlorophenyl)-1H-pyrazol-3-yl)phenyl) morpholine (S)-2-(4-(5-(3-Chlorophenyl)-1H-pyrazol-3-yl)phenyl) morpholine 3-[5-(4-Morpholin-2-yl-phenyl)-2H-pyrazol-3-yl]-benzonitrile (S)-2-(4-(5-(2,4-Difluorophenyl)-1H-pyrazol-3-yl)phenyl)morpholine (R)-2-(4-(5-(2,4-Difluorophenyl)-1H-pyrazol-3-yl)phenyl)morpholine (S)-2-(4-(5-(Tetrahydro-2H-pyran-4-yl)-1H-pyrazol-3-yl) phenyl)morpholine (S)-4-(3-(4-(Morpholin-2-yl)phenyl)-1H-pyrazol-5-yl)benzonitrile
(S)-2-(4-(5-(4-Fluorophenyl)-1H-pyrazol-3-yl)phenyl)morpholine
(S)-4-Fluoro-N-(3-(4-(morpholin-2-yl)phenyl)-1H-pyrazol-5-yl)benzamide
(R)-2-(4-(5-(4-Fluorophenyl)-1H-pyrazol-3-yl)phenyl)morpholine
(R)-4-(3-(4-(Morpholin-2-yl)phenyl)-1H-pyrazol-5-yl)benzonitrile
(S)-3-Fluoro-4-(3-(4-(morpholin-2-yl)phenyl)-1H-pyrazol-5-yl)benzonitrile
(S)-2-{4-[5-(6-Chloro-pyridin-3-yl)-1H-pyrazol-3-yl]-phenyl}-morpholine
(R)-2-{4-[5-(6-Chloro-pyridin-3-yl)-1H-pyrazol-3-yl]-phenyl}-morpholine
(S)-2-(3-Fluoro-4-(5-(4-fluorophenyl)-1H-pyrazol-3-yl)phenyl)morpholine
(R)-2-(3-Fluoro-4-(5-(4-fluorophenyl)-1H-pyrazol-3-yl)phenyl)morpholine
(S)-2-(4-(5-(2-Chloropyridin-4-yl)-1H-pyrazol-3-yl)phenyl)morpholine.
(S)-2-(4-(6-bromo-1H-imidazo[4,5-b]pyridin-2-yl)phenyl)morpholine.
(S)-2-(4-(5-(4-Fluorophenyl)-1,3,4-oxadiazol-2-yl)phenyl)morpholine
(R)-2-(4-(5-(4-Fluorophenyl)-1,3,4-oxadiazol-2-yl)phenyl)morpholine.
(S)-2-(4-(1-(4-Fluorophenyl)-1H-1,2,3-triazol-4-yl)phenyl)morpholine
(R)-2-(4-(1-(4-Fluorophenyl)-1H-1,2,3-triazol-4-yl)phenyl)morpholine.
(S)-2-(4-(1-(4-Fluorophenyl)-1H-pyrazol-4-yl)phenyl)morpholine
(R)-2-(4-(1-(4-Fluorophenyl)-1-pyrazol-4-yl)phenyl)morpholine.
(S)-2-(4-(5-(4-Fluorophenyl)-1H-1,2,4-triazol-3-yl)phenyl)morpholine
(R)-2-(4-(5-(4-Fluorophenyl)-1H-1,2,4-triazol-3-yl)phenyl)morpholine.
(S)-2-(4-(3-(4-Fluorophenyl)-1H-1,2,4-triazol-1-yl)phenyl)morpholine
(R)-2-(4-(3-(4-Fluorophenyl)-1H-1,2,4-triazol-1-yl)phenyl)morpholine.
(S)-2-(4-(4-(4-Fluorophenyl)-1H-1,2,3-triazol-1-yl)phenyl)morpholine
(R)-2-(4-(4-(4-Fluorophenyl)-1-1,2,3-triazol-1-yl)phenyl)morpholine.
(S)-2-{4[®-4-(4-Fluoro-phenyl)-4,5-dihydro-oxazol-2-yl]-phenyl}-morpholine.
(S)-2-(2-(4-Fluorophenyl)-1H-benzo[d]imidazol-5-yl)morpholine
(R)-2-(2-(4-Fluorophenyl)-1H-benzo[d]imidazol-5-yl)morpholine.
4-Fluoro-N-(6-(morpholin-2-yl)-1H-indazol-3-yl)benzamide.
(S)-2-(9H-Pyrido[2,3-b]indol-6-yl)morpholine
(S)-2-(3-(Trifluoromethyl)-9H-pyrido[2,3-b]indol-6-yl)morpholine
(S)-2-(3-Chloro-9H-pyrido[2,3-b]indol-6-yl)morpholine
(R)-2-(3-(Trifluoromethyl)-9H-pyrido[2,3-b]indol-6-yl)morpholine
(S)-2-(2-(Trifluoromethyl)-9H-pyrido[2,3-b]indol-6-yl)morpholine
(R)-2-(3-(Trifluoromethyl)-9H-pyrido[2,3-b]indol-6-yl)morpholine
(S)-2-(2-Isopropoxy-9H-pyrimido[4,5-b]indol-6-yl)morpholine
(R)-2-(6-Ethoxypyridin-3-yl)-6-(morpholin-2-yl)benzo[d]oxazole
(R)-6-(Morpholin-2-yl)-2-(6-(trifluoromethyl)pyridin-3-yl)benzo[d]oxazole
(R)-6-(Morpholin-2-yl)-2-(2-(trifluoromethyl)pyridin-4-yl)benzo[d]oxazole or
(S)-6-(Morpholin-2-yl)-2-(2-(trifluoromethyl)pyridin-4-yl)benzo[d]oxazole.

18. A process for the manufacture of a compound of formula I as defined in claim 1, which process comprises deprotecting a compound of formula

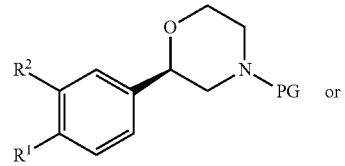

2-1

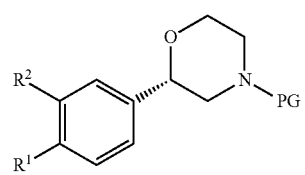

2-2 with HCl in dioxane for 2 hours at 60° C., or with CF$_3$COOH in dichloromethane at room temperature to a compound of formula

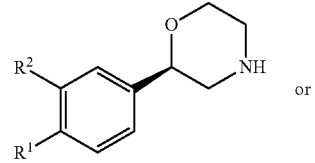

I-1

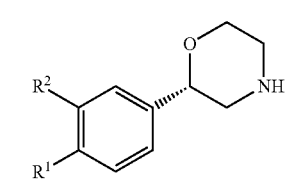

I-2 wherein PG is an acid labile amino protecting group, selected from tert-butoxycarbonyl, and R$^1$ and R$^2$ are as described in claim 1 and,
if desired, converting the compounds obtained into pharmaceutically acceptable acid.

19. A compound according to claim 1, when manufactured by a process according to claim 18.

20. A pharmaceutical composition comprising a compound of claim 1 and a pharmaceutical acceptable carrier and/or adjuvant.

21. A pharmaceutical composition comprising a compound of claim 1 and a pharmaceutical acceptable carrier and/or adjuvant for use in the treatment of depression, anxiety disorders, bipolar disorder, attention deficit hyperactivity disorder (ADHD), stress-related disorders, psychotic disorders, schizophrenia, neurological diseases, Parkinson's disease, neurodegenerative disorders, Alzheimer's disease, epilepsy, migraine, hypertension, substance abuse, metabolic disorders, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

* * * * *